United States Patent [19]

Tao et al.

[11] Patent Number: 5,324,638
[45] Date of Patent: Jun. 28, 1994

[54] BRAIN TRANSCRIPTION FACTOR, NUCLEIC ACIDS ENCODING SAME AND USES THEREOF

[75] Inventors: Wufan Tao; Eseng Lai, both of New York, N.Y.

[73] Assignee: Sloan-Kettering Institute for Cancer Research, New York, N.Y.

[21] Appl. No.: 882,292

[22] Filed: May 13, 1992

[51] Int. Cl.$^5$ .................. C12P 21/06; C07K 13/00
[52] U.S. Cl. .................. 435/69.1; 536/23.5; 530/350
[58] Field of Search .............. 536/27; 435/69.1, 320.1; 53/350

[56] References Cited

PUBLICATIONS

Costa, R., et al. Multiple Hepatocyte-Enriched Nuclear Factors Function in the Regulation of Transthyretin and Alpha1-Antitrypsin Genes. Molecular and Cellular Biology 9: 1415–1425, 1989 (Exhibit B).

Courey, A. J. and Tjian, R. Analysis of Sp1 In Vivo Reveals Multiple Transcriptional Domains, Including a Novel Glutamine-Rich Activation Motif. Cell 55; 887–898, 1988 (Exhibit C).

Davis, C. A., et al. Expression of the Homeobox-Containing Gene En-2 Delineates a Specific Region of the Developing Mouse Brain. Genes & Development 2: 361–371, 1988 (Exhibit D).

Davis, C. A. and Joyner, A. L. Expression of the Homeo Box-Containing Genes En-1 and En-2 and the Proto-oncogene int-1 Diverge During Mouse Development. Genes & Development 2: 1736–1744, 1988 (Exhibit E).

He, X., et al. Expression of a Large Family of POU-Domain Regulatory Genes in Mammalian Brain Development. Nature 340: 35–42, 1989 (Exhibit F).

He, X. and Rosenfeld, M. G. Mechanisms of Complex Transcriptional Regulation: Implications for Brain Development. Neuron 7: 183–196, 1991 (Exhibit G).

Kessel, M. and Gruss, P. Murine Developmental Control Genes. Science 249; 374–379, 1990 (Exhibit H).

Lai, E., et al. HNF-3A, A Hepatocyte-Enriched Transcription Factor of Novel Structure is Regulated Transcriptionally. Genes & Development 4: 1427–1436 1990 (Exhibit I).

Lai, E., et al. Hepatocyte Nuclear Factor 3 α Belongs to a Gene Family in Mammals that is Homologous to the Drosophila Homeotic Gene Fork Head. Genes & Development 5: 416–427 (Exhibit J).

Li, C., et al. Cloning of a Cellular Factor, Interleukin Binding Factor, that Binds to NFAT-Like Motifs in the Human Immunodeficiency Virus Long Terminal Repeat. Proc. Natl. Acad. Sci. USA 88: 7739–7743, 1991 (Exhibit K).

Mermod, N., et al. The Proline-Rich Transcriptional Activator of CTF/NF-1 is Distinct From the Replication and DNA Binding Domain. Cell 58: 741–753, 1991 (Exhibit L).

Mori, K., et al. Telencephalon-Specific Antigen Identified by Monoclonal Antibody, Proc. Natl. Acad. Sci. USA 84: 3921–3925, 1987 (Exhibit M).

Price, M., et al. A Mouse Gene Related to Distal-less Shows a Restricted Expression in the Development Forebrain. Nature 351: 748–750, 1991 (Exhibit N).

Weigel, D. and Jackel, H. The Fork Head Domain: A Novel DNA Binding Motif of Eucaryotic Transcription Factors?Cell 63: 455–456, 1990 (Exhibit O).

Wilkinson, D. G., et al. Segmental Expression of Hox-2 Homeobox-Containing Genes in the Developing Mouse Hindbrain. Nature 341: 405–409, 1989 (Exhibit P).

*Primary Examiner*—Robert J. Hill, Jr.
*Assistant Examiner*—K. Cochrane Carlson
*Attorney, Agent, or Firm*—John P. White

[57] ABSTRACT

This invention provides an isolated, purified transcription factor expressed in the telencephalic region of the brain of a developing animal or in structures derived therefrom. Also provided is a nucleic acid molecule, e.g., an RNA or a DNA molecule encoding the transcription factor of this invention. Further provided are a pharmaceutical composition comprising the transcription factor and a method of correcting an animal's defective synthesis of the transcription factor which comprises administering to the patient an effective amount of the pharmaceutical composition. Still further provided are an expression vector containing this nucleic acid molecule, a host vector system containing the vector and a method of producing the transcription factor comprising growing the host vector system under suitable conditions.

This invention provides methods of diagnosing the overexpression of the transcription factor in tissue in which it is normally expressed and of detecting the presence of the factor in tissue.

9 Claims, 12 Drawing Sheets

FIGURE 1-1

```
GGCGGCCGCTCCGGGACGCGCCGCTCTCCCCCCTTCGGGCTGCCGCTGCTGTGACT              76
GCTGCGGGCGCGAGGAGGAGGAGGCGGGGAGGCGGGCGGAACGCGGGCCTGCACCCCGGGC        154
GACGGGTTGCTTCTGCCTCTAGTCTTGAGGGGTGGTTGCAGCTTTTGCTACATGCCTTGC        232
TCTCTCTCTAATTCTTGAGGGGTGGTTGCAGCTTTTGCTACATGCCTGGCGGTCCAACTGCG      310
CTGCTGCCGAGCGCTCAGTGCCCCCGCCGCCCCACTCCCCCCCCGGGCCCGAACCCGGTCGCCG    388
CGCTGCTCGGCTCCTGCGCGCCCGCCGTCCTGCGCGCCGACGCGCTGGGTGATGCTGGACATGGGAGATAGGAAA  466
                                            M  L  D  M  G  D  R  K    8
GAGGTGAAAATGATTCCCAAGTCCTCGTTCAGCATCAACAGCCTGGTCCCTGAGGCCGTCCAGAACGACAACCACCAC  544
E  V  K  M  I  P  K  S  S  F  S  I  N  S  L  V  P  E  A  V  Q  N  D  N  H  H   34
GCGAGCCACGGTCACCACAACAGCCACCCCCAGCCATCACCATCATCACCACCACCCGCCCCCGCCC          622
A  S  H  G  H  H  N  S  H  H  P  Q  H  H  H  H  H  H  H  P  P  P  P            60
GCGCCTCAGCGCCGCCACCGCCACCGCCAGCAGCAGCAGCCCCCCGCCGCCCCCCAGGCCCCAGGCCGGCGGC      700
A  P  Q  R  R  H  R  H  R  Q  Q  Q  Q  P  P  A  P  Q  P  P  Q  A  R  G         86
GCCCCAGCAGCGGACGACGACAAGGGCCCCCAGCCGCCTTCTGCTCCCGGCCTTCCGCCAGGCT              778
A  P  A  A  D  D  D  K  G  P  Q  P  L  L  P  P  S  A  A  L  D  G  A  K  A       112
GACGCACTTGGAGCCAAAGGCGAGCCAGGGGGCGGCCCTGCGGAGCTGGCGCCCGTGGGCCCGGACGAGAAGGAGAAG  856
D  A  L  G  A  K  G  E  P  G  G  G  P  A  E  L  A  P  V  G  P  D  E  K  E  K    138
GGCGGCGGCGCTGGGGAGGAGAAGAAGGGCGCGGAGGGGCGCGAGGGGCAAGGAGGAGGGCGAC              934
G  A  G  G  E  E  K  K  G  A  G  E  G  G  G  K  D  G  E  G  G  K  E  G  D       164
```

FIGURE 1-2

```
AAGAAGAACGGCAAGTACGAGAAGCCGCCGTTCAGCTACAACGCCCTCATCATGATGGCCATCAGGCAGAGTCCCGAG    1012
 K  K  N  G  K  Y  E  K  P  P  F  S  Y  N  A  L  I  M  M  A  I  R  Q  S  P  E      190

AAGCGCCTGACGCTCAACGGCATCTACGAGTTCATCATGAAGAACTTCCCTTACTACCGCGAGAACAAGCAGGGCTGG    1090
 K  R  L  T  L  N  G  I  Y  E  F  L  M  K  N  F  P  Y  Y  R  E  N  K  Q  G  W      216

CAGAACTCCATCCGCCACAACCTGTCCCTCAACAAGTGCTTCGTGAAGGTACCGCGCCACTACGACGACCCGGGCAAG    1168
 Q  N  S  I  R  H  N  L  S  L  N  K  C  F  V  K  V  P  R  H  Y  D  D  P  G  K      242

GGCAACTACTGGATGCTGGACCCGTCGAGCGACGACGTGTTCATCGGCGGCACGACCGGCAAGCTGCGGCGCCGCTCC    1246
 G  N  Y  W  M  L  D  P  S  S  D  D  V  F  I  G  G  T  T  G  K  L  R  R  R  S      268

ACCACGTCTCGGGCCAAGCTAGCCTTTAAGCGCGGGGCACGGCTCACCTCCACCGGCCTCACCTTCATGGACCGCGCC    1324
 T  T  S  R  A  K  L  A  F  K  R  G  A  R  L  T  S  T  G  L  T  F  M  D  R  A      294

GGCTCCCTCTACTGGCCCATGTCGCCCTTCCTGTCCCTGCACCACCCTCGCGCCAGCAGCACTTTGAGTTACAACGGG    1402
 G  S  L  Y  W  P  M  S  P  F  L  S  L  H  H  P  R  A  S  S  T  L  S  Y  N  G      320

ACCACGTCGGCCTACCCGAGCCACCCCATGCCCTACAGTCCCGTGTTGACTCAAAACTCGCTGGGCAACAACCACTCC    1480
 T  T  S  A  Y  P  S  H  P  M  P  Y  S  S  V  L  T  Q  N  S  L  G  N  N  H  S      346

TTCTCCACCGCCAACGGGCTGAGCGTGGACCGGCTGGTCAACGGGGAGATCCCGTACGCCACGCACCACCTCACGGCC    1558
 F  S  T  A  N  G  L  S  V  D  R  L  V  N  G  E  I  P  Y  A  T  H  H  L  T  A      372
```

FIGURE 1-3

```
GCTGGCTCCGCCGCCTCCGTCCGCGGCCTGTCCGTCGGTGCCCTGTCCGGGACCTACTCCCTGAACCCCTGTCCGTC    1636
 A  L  A  A  S  V  P  C  G  L  S  V  P  C  S  G  T  Y  S  L  N  P  C  S  V         398

AACCTGCTCGCGGGCCAGACCAGTTACTTTTTCCCCCACGTCCCCACGTCAATGACTTCGCAGACCAGCACGTCC        1714
 N  L  A  G  Q  T  S  Y  F  F  P  H  V  P  H  P  S  M  T  S  Q  T  S  T  S          424

ATGAGCGCCCGGGCCGCGTCCTCCTACGTCGCCAGGCCCCCCTGACCCTGCCCTGTAGTCTTTAAGACCCTCT          1792
 M  S  A  R  A  A  S  S  T  S  P  Q  A  P  S  T  L  P  C  E  S  L  R  P  S         450

TTGCCAAGTTTTACGACAGGACTGTCCGGGGACTGTCTGATTATTCACACATCAAAATCAGGGTCTCTTCTCCAAC      1870
 L  P  S  F  T  T  G  L  S  G  G  L  S  D  Y  F  F  T  H  Q  N  Q  G  S  S  N      476

CCTTTAATACATTAACATCCCGGGACCAGACTGTAAGTGAACGTTTACACACATTTGCATTGTAAATGATAATTAA      1948
 P  L  I  H  *                                                                      480

AAATAAGTCCAGGTATTTTTATTAAGCCCTTCCCCCATTTCTGTACGTTTGTTCAGTCTTTAGGGTTGTTTACTA        2026
TTCTAACACGGTTGGAGTGTCAGCAGCGAGGTGCAATGTGGGAGAATACATTGTAGAATATAAGGTTTGGACGTCAA      2104
ATTATAGTAGAATGTGTATCTAAATAGTGACTGCTTTGCCATTTCATTCAAACCTGACAAGTCTATCTCTAAAGGCTG    2182
CCAGATTTCCATGTGTGCAGTATTATAGTATCATGGATCTATCTGGTGACGCAGGCCTTGAAGAACAACCTAAAT       2260
TATGAAGAGAGTTTTAAATGTTAAACTGTTAATTTGTATTTAAGAATTGTAGTAAGGTGCCAAGAAATTATATTG      2338
GCCATTTATTGTTTTGTCCTTTTAAAGAACTGTTTTTTCCTTTGTTTTACTTTTAGACAACAAAGATTGGATTCT      2416
AGCAAATGCACTTGGTATACTAAGTATTAAAACAAGCAAACAAAAAAGGAAGTTGTTTAGTTTGGCAA              2494
CACTGCCCATTCAATTGAATCCGAAAGGACAAAATTAAGGATTGCCTTCAGTTGTGTTGTATATTCGATGTATG        2572
TGGTCACTAACAGGTCACTTTTATTTTCTAAATGTAGTGAAATGTTAATACCTATTGTACTTATAGTAAACCTTG       2650
CAAATATGTAACCTGTGTTGCCGCAAATGCCGCATCAATTTGAGTGATTGTTAATGTGTCTTAAAATTCTTGATTGT     2728
GATACTGTGGTCATATGCCCTGTCTTGTGTCACTTACAAAAATGTTTACTATGAACACACAGAAATAAAAAATAGGCTAA  2806
ATTCATATATAAAAAAAAAAAAAA                                                            2832
```

FIGURE 5A
FIGURE 5B
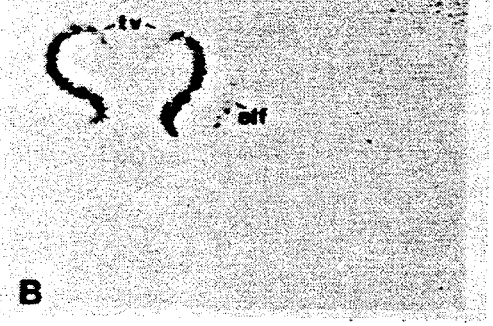
FIGURE 5C       FIGURE 5D
 

BRAIN TRANSCRIPTION FACTOR, NUCLEIC ACIDS ENCODING SAME AND USES THEREOF

BACKGROUND OF THE INVENTION

One of the important early events in the development of the mammalian central nervous system is the establishment of regional diversity along the neural tube under the influence of signals from the underlying mesoderm (Mangold 1933; Spemann 1938; Placzek et al. 1990). The caudal portion of the neural tube gives rise to the spinal cord while the rostral part develops into the brain. Morphologic studies have identified the initial subdivision of the developing brain into three vesicles, the forebrain, midbrain and hindbrain. The forebrain and hindbrain subsequently each subdivide, resulting in the five major regions of the brain. The most rostral region, the telencephalon, gives rise to the structures of the cerebral hemispheres which include the cerebral cortex and basal ganglia (Kandel et al. 1991). This subdivision of the developing brain is apparent initially as changes in the shape of the neuroepithelium, and is established prior to differentiation of the progenitor cells into neurons and glia (McKay 1989).

Our understanding of the molecular events which establish the regional subdivision of the brain during mammalian development have been aided by several approaches. Because development depends on the expression of genes in distinct spatial and temporal patterns, one approach has been the study of transcription factors which control gene expression in a cell or tissue-specific fashion. Another approach is the identification of mammalian homologs of Drosophila genes which have been established to play crucial roles in insect development (Kessel and Gruss 1990). For example, homeobox gene complexes in Drosophila and mammals are strikingly similar in structural organization and expression pattern along the A-P axis of the organism (Duboule and Dolle 1989; Graham et al. 1989). While recent findings of restricted expression in the developing brain of several homeodomain and one zinc finger proteins have provided insight into the development of the hindbrain (Murphy et al. 1989; Wilkinson et al. 1989; Wilkinson et al. 1989; Hunt et al. 1991). The molecular basis of forebrain development remains poorly understood.

We have recently described a novel family of transcriptional activators, the HNF-3 family, whose members function to stimulate expression of a group of liver-specific genes. The expression of these factors in the mature animal is limited to tissues which derive from the gut endoderm such as the liver, lung and intestine (Lai et a. 1991). These findings suggested that HNF-3 family members might play a significant role in the development of these tissues. This hypothesis was supported when we learned that HNF-3 proteins were highly homologous to a Drosophila protein, fork head, which had been shown to be critical to normal fly development and to be expressed in the cells which were to form the insect gut structures (Weigel et al. 1989; Weigel and Jackle 1990). In this paper we describe the discovery of a new member of the HNF-3/fork head family of transcription factors which is unique in that its expression is restricted to the telencephalon of the developing rat brain. Expression is readily detectable by embryonic day 10 in the area of the neural tube which gives rise to the telencephalic vesicles suggesting a critical role for this factor in the development of this region of the forebrain.

SUMMARY OF THE INVENTION

This invention provides an isolated, purified transcription factor expressed in the telencephalic region of the brain of a developing animal or in structures derived therefrom. Also provided is a nucleic acid molecule, e.g., an RNA or a DNA molecule encoding the transcription factor of this invention. Further provided are a pharmaceutical composition comprising the transcription factor and a method of correcting an animal's defective synthesis of the transcription factor which comprises administering to the patient an effective amount of the pharmaceutical composition. Still further provided are an expression vector comprising this nucleic acid molecule, a host vector system comprising the vector and a method of producing the transcription factor comprising growing the host vector system under suitable conditions.

This invention provides methods of detecting the expression of the transcription factor in tissue in which the factor is normally expressed, of diagnosing the abnormal expression of the transcription factor in tissue, of defecting the presence of the factor in tissue and of correcting an animal's defective synthesis of the transcription factor.

BRIEF DESCRIPTION OF THE DRAWINGS

FIGS. 1-1, 1-2, and 1-3 Nucleic acid sequence of BF-1 (SEQ ID No. 1). The protein sequence is shown below beginning with the initiator methionine at base 443. The DNA binding domain homology extends from amino acid 162-271. Underlined amino acids are identical to those in the DNA binding domain of at least two of the four previously identified members of the HNF-3/fork head family.

FIG. 2 Translation of the BF-1 protein in reticulocyte lysates from transcripts synthesized in vitro from the full length BF-1 template (lane 1), or templates deleting the 5' end of the cDNA 150 bp, BF-1δ150 (lane 2) or 331 bp, BF-1δ331 (lane 3). The size of the major product is the same for all three, demonstrating that the initiation site lies downstream of nucleotide 331. The lower MW products represent internal initiations, while the minor higher MW product present with templates BF-1 and BF-1δ150 represents initiation at an upstream GUG at neucleotide 254. As expected, this higher MW product is absent with template BF-1δ331. These additional products are attributable to the more permissible initiations which occur in reticulocyte lysates.

FIG. 3 Northern analysis of poly A+ RNA from adult (A) and E17 fetal (F) rat tissues. One major mRNA species is detected in the brain at 2.9 kB, with a probe for BF-1. A minor band is seen at 5 kB. This mRNA is not detected in the other tissues even with prolonged exposure of the blot. The same blot was reprobed with GAPDH to assess the quantity of RNA. Sm INT-small intestine.

FIGS. 5A–5K Expression pattern of BF-1 during rat development assessed by in-situ hybridization with an antisense probe (A-H, J-M). Pairs of photomicrographs and the corresponding autoradiograph from a transverse section of an E11.5 embryo (A, B), sagittal section of an E15 embryo (C, D) and a sagittal section of an E17 brain (E, F). Arrowheads in E indicate the approximate level of coronal sections (G,G) whose autoradiographs are shown. I is a representative control autoradiograph of a section parallel to that shown in E, hybridized with the corresponding sense probe for BF-1. J and K are autoradiographs of sagittal and coronal sections from adult brain. t, Telencephalon; d, diencephalon; ms, mesencephalon; mt, metencephalon; my, myelencephalon; s, spinal cord; cor, cerebral cortex; cb, cerebellum; cp, caudate putamen; h, hippocampus; tv, telencephalic vesicle; lv, lateral ventricles,; op, optic stalk; r, retinal neuroepithelium; olf, olfactory placode; ole, olfactory epithelium; fg, foregut.

DETAILED DESCRIPTION OF THE INVENTION

Figure 2:
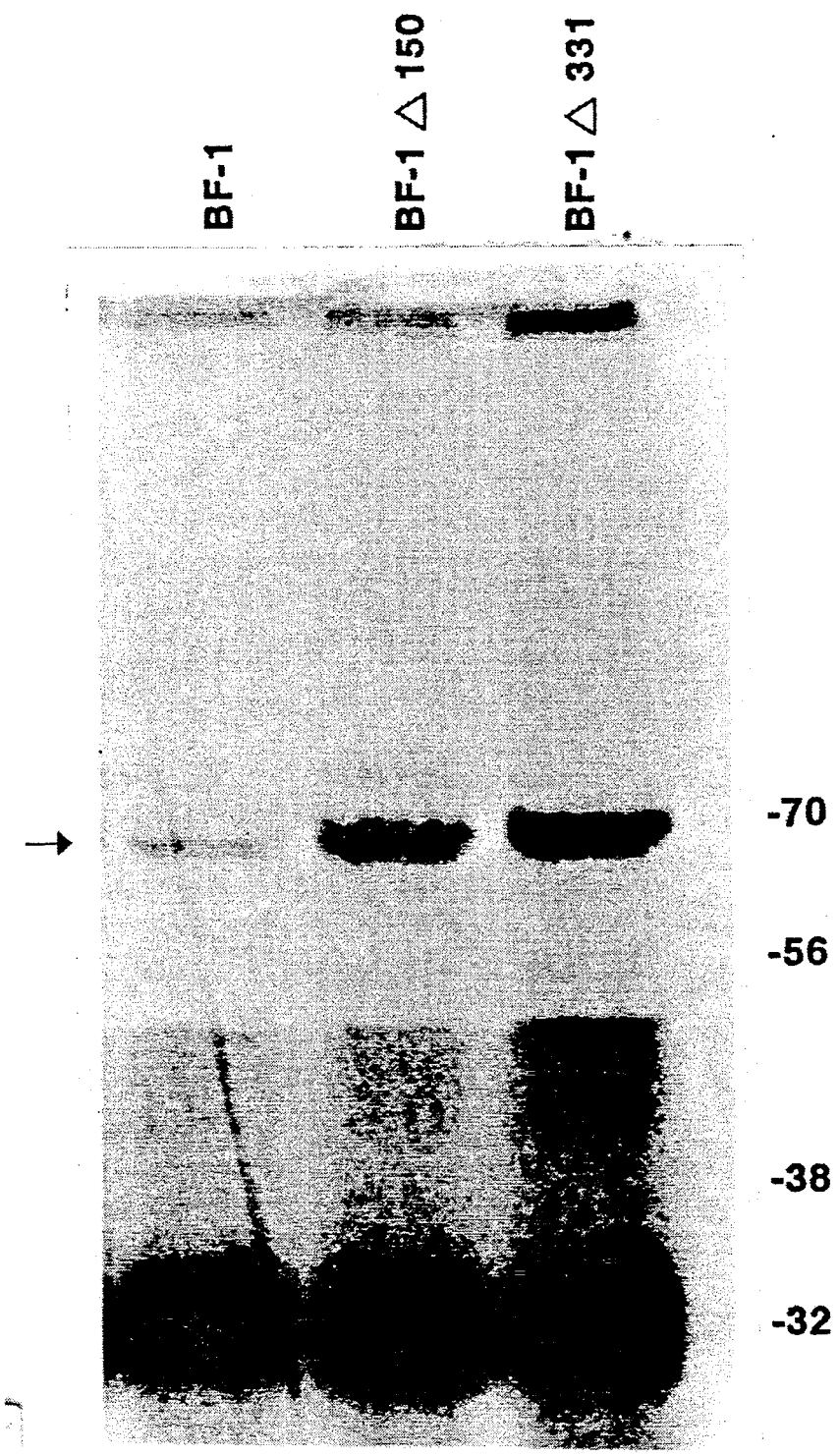

This invention provides an isolated, purified transcription factor expressed in the telencephalic region of the brain of a developing animal or in structures derived therefrom. For the purposes of this invention, an "isolated, purified" transcription factor is a nonnaturally occurring transcription factor, i.e., a transcription factor in a form which does not occur in nature. The term "transcription factor" as used herein means a protein whose presence is required to assist eucaryotic polymerases in starting RNA synthesis at correct sites on the DNA. The transcription factor may be a RNA polymerase II transcription factor, i.e., a factor which enables RNA polymerase II to start synthesis of mRNA at correct sites on the DNA. In one embodiment of this invention, the animal is a mammal, e.g., a mouse, rat or human.

The transcription factor of this invention is expressed in the telencephalon of the embryo of an animal and is also expressed, at a lower level, in the telencephalon-derived structures in the adult. The transcription factor of this invention is expressed in the cerebral hemispheres of the adult brain. The isolated, purified transcription factor provided by this invention may have the amino acid sequence shown in FIG. 1 (SEQ ID No. 2).

This invention also provides a protein which comprises an amino acid sequence fused to the isolated, purified transcription factor of claim 1 or to a fragment of the transcription factor. In one embodiment of this invention, the amino acid sequence is derived from glutathione transferase. In the presently preferred embodiment of this invention, the fragment of the transcription factor to which the amino acid sequence is fused corresponds to the DNA binding domain of the transcription factor.

This invention further provides a pharmaceutical composition comprising the transcription factor of this invention and a suitable carrier. Suitable carriers for a transcription factor are well known to those of ordinary skill in the art and include, but are not limited to, aqueous buffers. This invention still further provides a method of correcting an animal's defective synthesis of a transcription factor expressed in telencephalon-derived structures which comprises administering to the animal an effective amount of the pharmaceutical composition of this invention. "Correcting" an animal's defective synthesis of a transcription factor as used herein is intended to mean supplying the animal with an exogenous source of transcription factor when the animal itself synthesizes an insufficient amount of the transcription factor to meet its physiological needs. An "effective amount" of the pharmaceutical compositions in any amount of the composition effective to supply the animal with the transcription factor which the animal synthesizes in insufficient amounts. Methods of determining an effective amount are well known to those skilled in the art or can readily be determined by routine experimentation.

This invention provides an isolated nucleic acid molecule encoding the transcription factor of this invention. In one embodiment of this invention, the nucleic acid molecule is a messenger RNA molecule. In another embodiment of this invention, the nucleic acid molecule is a DNA molecule. The DNA molecule of this invention may be a cDNA molecule, e.g., a cDNA molecule having a nucleotide sequence substantially the same as the neucleotide sequence shown in FIG. 1 (SEQ ID No. 1). The cDNA molecule may be labelled with a detectable marker, e.g., a radioisotope. The DNA molecule of this invention may also be a genomic DNA molecule.

Applicants have isolated a genomic DNA molecule which is approximately 20 kb in length ad which includes all of the exons of the gene for the transcription factor. The genomic DNA molecule provided by this invention contains, in addition to the exons, DNA sequences which are involved with regulating the expression of the gene. These DNA sequences may be sequences to which factors bind that either promote or inhibit the expression of the gene. An example of such a factor is a growth factor. Accordingly, "correcting" an animal's defective synthesis of a transcription factor as used herein also means modulating the expression of the gene encoding the transcription factor. Such expression may be modulated by administering factors to the animal which either promote or inhibit expression of the gene. The ability of factors to promote or inhibit gene expression may be dependent on their ability to bind to DNA sequences which regulate gene expression. Such sequences involved in the regulation of the gene encoding the transcription factor of this invention are present in applicant's isolated genomic DNA molecule.

This invention provides a method of detecting the expression in the telencephalon-derived tissue of an animal of a transcription factor normally expressed in such tissue which comprises the steps of: isolating a sample of telencephalon-derived tissue from the animal; contacting the tissue sample with a labelled probe derived from the cDNA molecule of this invention under conditions permitting the probe to bind to mRNA encoding the transcription factor; removing unbound probe from the tissue sample; and detecting the presence of bound, labelled probe in the tissue sample, said presence indicating the expression of the transcription factor in the telencephalon-derived tissue. The animal may be a mammal, e.g., a mouse, rat or human. Methods of isolating telencephalon derive tissue from an animal are well known to those skilled in the art. Methods of contacting tissue samples with cDNA probes, conditions suitable for binding of cDNA probes to mRNA in a tissue sample and methods of removing unbound probe from a sample are also well known to those skilled in the art. Additionally, methods of detecting bound, labelled probe in a tissue sample are well known to those skilled in the art.

This invention also provides a method of diagnosing the abnormal expression of a transcription factor normally expressed in telencephalon-derived tissue which comprises the steps of: isolating a sample of tissue from the animal; contacting the tissue sample with a labelled probe derived from the cDNA molecule of this invention under conditions permitting the probe to bind to mRNA in the tissue sample; removing unbound probe from the sample; detecting the presence of bound, labelled probe in the sample; quantifying the amount of bound, labelled probe in the sample; and comparing the amount of bound, labelled probe in the sample to the amount of labelled probe which binds to a sample of non telencephalon-derived tissue or to a sample of telencephalon-derived tissue from a subject which expresses normal levels of the transcription factor in such tissue. Methods of isolating sample of telencephalon-derived tissue, of contacting such tissue with a labelled probe under conditions permitting binding of the probe to mRNA in the sample and of removing unbound probe from the sample are well known to those skilled in the art or can readily be determined by routine experimentation. Methods of detecting and quantifying the amount of bound, labelled probe in a sample are also well known to those skilled in the art. The transcription factor of this invention is not normally expressed in non telencephalon-derived tissue. Identification of the transcription factor in such tissue is indicative of abnormal gene expression in the tissue. Comparison of the amount of bound, labelled probe in a sample of telencephalon-derived tissue from a subject animal with a similar sample from a normal animal will indicate whether the subject animal expresses an abnormal amount of the transcription factor of this invention. The presence of abnormal amounts of the transcription factor of this invention is related to the presence of an abnormal developmental state in the cells of telencephalon-derived tissue in which the transcription factor is expressed. The method provided by this invention is therefore useful in diagnosing the existence of an abnormal developmental state in the telencephalon derived tissue of an animal. Such animals include, but are not limited to mammals, e.g., mice, rats or humans.

This invention provides an expression vector comprising the isolated DNA molecule of this invention operably linked to a RNA polymerase promoter. Examples of such expression vectors include, but are not limited to, plasmids, viruses, cosmids or phages.

This invention provides a method of correcting an animal's defective synthesis of a transcription factor expressed in telencephalon-derived structures which comprises the steps of: isolating suitable cells from the animal; inserting the expression vector of this invention into the cells under conditions permitting stable integration of the vector into the genome of the cells and expression of the DNA molecule; and reintroducing the cells into the animal from which they were isolated. Cells suitable for use in accordance with the practice of this invention are well known to those skilled in the art or can readily be determined by routine experimentation. Methods of isolating such cells, and of readministering the cells to the animal, are also well known to those skilled in the art. "Inserting" an expression vectors as used herein is intended to mean any commonly accepted method of introducing an expression vector into cells such that the vector will stably integrate into the genome of the cell in a manner permitting the expression of the isolated DNA molecule in the integrated vector. Examples of such methods include, but are not limited to, calcium phosphate precipitation, electroporation or microinjection.

This invention also provides a method of correcting an animal's defective synthesis of a transcription factor expressed in telencephalon-derived structures which comprises the steps of: introducing the expression vector of this invention into a neuroepithelial cell line under conditions permitting stable integration of the vector into the genome of the neuroepithelial cells; and administering the neuroepithelial cells to the animal under conditions permitting the cells to grow in the animal and synthesize the transcription factor encoded by the expression vector. "Introducing" a vector into a cell in accordance with the practice of this invention is intended to mean any commonly accepted practice of introducing an expression vector into cells such that the vector will stably integrate into the genome of the cell in a manner permitting the expression of the isolated DNA molecule in the integrated vector. Examples of such methods include, but are not limited to, calcium phosphate precipitation, electroporation or microinjection. Neuroepithelial cells useful in accordance with the practice of this invention will be cells which can be administered to the animal without being rejected by the animal's immune system. Identification of such cells is within the purview of one of ordinary skill in the art. Methods of administering such cells are also well known to those skilled in the art.

This invention provides a host vector system comprising the expression vector of this invention in a suitable host cell. In one embodiment of this invention, the suitable host cell is a bacterial cell. In another embodiment of this invention, the suitable host cell is a eucaryotic cell.

This invention also provides a method of producing a transcription factor expressed in the telencephalic region of the brain of a developing vertebrate animal or in structures derived therefrom, which comprises growing the host vector system of this invention under conditions which permit transcription and translation, followed by recovering the protein so produced. Conditions permitting transcription and translation in a host vector system are well known to one of ordinary skill in the art or can readily be determined by routine experimentation. Methods of recovering proteins expressed by a host vector system are also well known to those skilled in the art.

This invention provides an antibody which specifically recognizes the transcription factor of this invention. The antibody may be labelled with a detectable marker. In one embodiment of this invention, the antibody is a monoclonal antibody. This invention also provides a hybridoma cell which produces the monoclonal antibody of this invention. This invention further provides a method of producing a monoclonal antibody which specifically recognizes a transcription factor expressed in the telencephalic region of the brain of a developing animal or in structures derived therefrom which comprises culturing the hybridoma cell of this invention under conditions permitting antibody production, followed by recovering the antibody so produced. Methods of culturing hybridomas to produce monoclonal antibodies and of recovering monoclonal antibodies produced by hybridomas are also well known to those skilled in the art or can readily be determined by routine experimentation.

This invention provides a pharmaceutical composition comprising the antibody of this invention and a suitable carrier. Suitable carriers are well known to those of skill in the art or can readily be determined by hem without undue experimentation. Examples of suitable carriers include, but are not limited to, aqueous buffers. This invention also provides a method of detecting the presence in an animal of a transcription factor normally expressed in the telencephalic region of the brain of a developing animal or in structures derived therefrom which comprises the steps of: isolating a sample of suitable tissue from the animal; contacting the sample with the pharmaceutical composition of this invention, wherein the antibody is labelled with a detectable marker, under conditions permitting the antibody to bind to transcription factor in the sample; removing unbound, labelled antibody from the sample; and detecting the presence of bound antibody in the sample, said presence indicating the presence of transcription factor in the tissue sample. Methods of isolating telencephalon-derived tissue from an animal, of contacting the tissue with a pharmaceutical composition comprising a labelled antibody under conditions permitting binding of the antibody to protein in the sample and of removing unbound antibody from the sample and of detecting bound, labelled antibody in the sample are well known to those skilled in the art or can readily be determined by them without undue experimentation.

This invention also provides a method of detecting the presence in a patient of tumors arising from telencephalic-derived tissue which comprises the steps of: (i) isolating a sample of tumor tissue from the patient; contacting the sample with an effective amount of the pharmaceutical composition of the antibody of this invention and a suitable carrier, wherein the antibody is labelled with a detectable marker, under conditions permitting the antibody to bind to transcription factor in the sample; removing unbound, labelled antibody from the sample; and detecting the presence of bound, labelled antibody in the sample, said presence indicating the presence of transcription factor and thereby the presence of a tumor arising from telencephalic-derived tissue. Methods of isolating tumor tissue from an animal, of contacting the tissue with a pharmaceutical composition comprising a labelled antibody under conditions permitting binding of the antibody to protein in the sample and of removing unbound antibody from the sample and of detecting bound, labelled antibody in the sample are well known to those skilled in the art or can readily be determined by them without undue experimentation.

This invention will be better understood from the Examples which follow. However, those skilled in the art will readily appreciate that the specific examples detailed are only illustrative of the invention as described more fully in the claims which follow thereafter.

Results

Isolation of cDNA Clones for BF-1

We knew that Drosophila fork head or a closely related protein is expressed in the central nervous system of Drosophila (Weigel, Jurgens et al. 1989) while the three HNF-3 proteins were not expressed in the mammalian brain (Lai, Prezioso et al. 1991). Therefore we postulated that additional members of the HNF-3 gene family, which were critical to the development of the central nervous system, would be expressed in the mammalian brain. Northern analysis using an HNF-3a probe which spanned the DNA binding domain, was performed at low stringency. This revealed a 2.9 kb RNA species from whole brain tissue which was no longer detected after a high stringency wash. This probe was then used to screen a rate whole brain lambda gt11 DNA library. From a screen of 500,000 recombinants, 10 positive clones were obtained of which 6 proved to be from the same cDNA as assessed by restriction and partial sequence analysis. One clone was 2.9 kb in length and contained an open reading frame (FIG. 1 (SEQ ID No. 1)) which encodes a protein of 480 amino acids, which we call BF-1 (brain factor-1). The ATG at 443 is the translation initiation start site. It is the first to have a purine at the $-3$ position (Kozak 1986), is preceded by an in-frame termination codon and deletions of up to 331 nucleotides of the 5' end of the cDNA do not alter the size of the protein translated in reticulocyte lysates from RNA transcribed in vitro using T7 or T3 RNA polymerase compared to that translated from the full length cDNA (FIG. 2). The translated protein of 480 amino acids migrates with an apparent molecular weight on SDS-polyacrylamide gels of 67,000 daltons. For comparison, the translated HNF-3a protein of 466 amino acids migrates with an apparent size of 60,000 daltons. This size is different than previously reported (Lai et al. 1990) because the pre-stained molecular weight markers we have been using were recently recalibrated by the manufacturer (Sigma) to be larger than previously indicated. Both proteins migrate on SDS-gels more slowly than expected from the calculated size.

Expression of BF-1 is Distinct From That of HNF-3a, 3b and 3g

Figure 3:
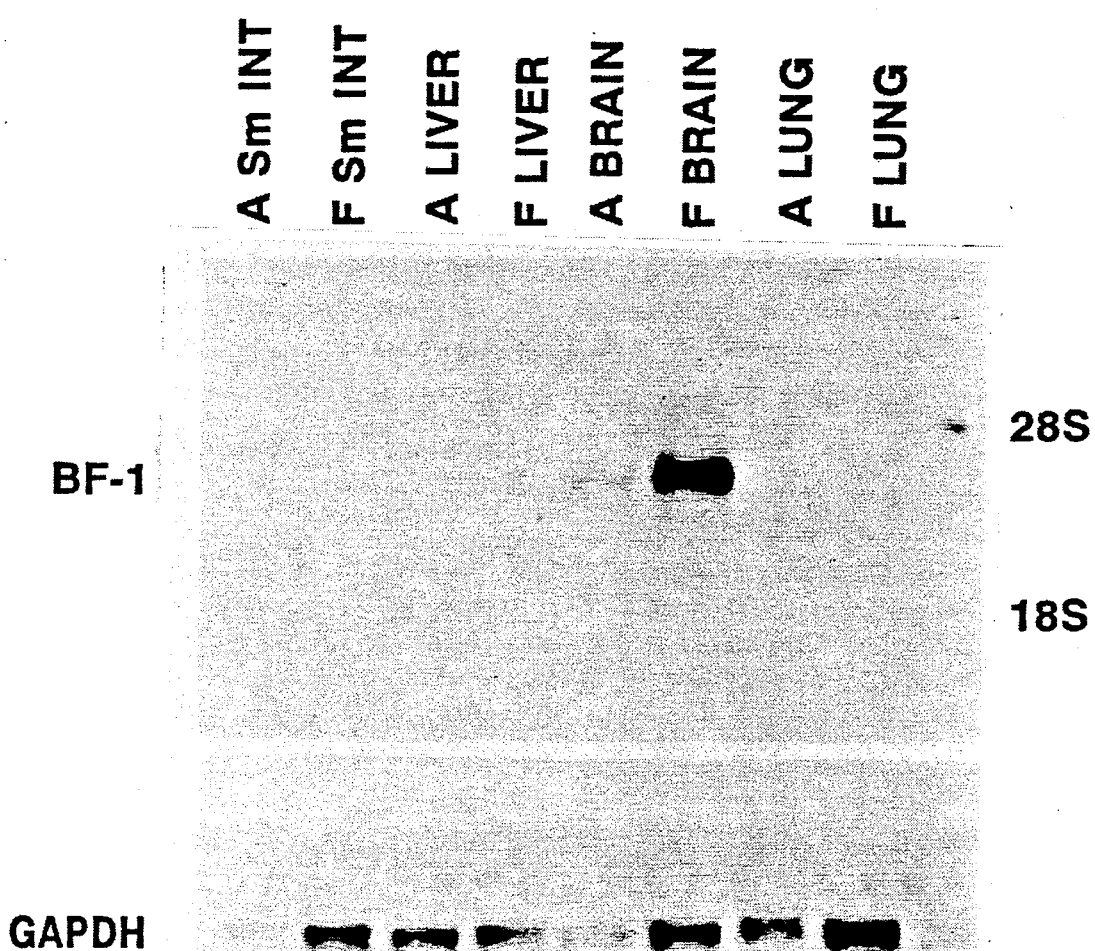
Figure 4B:
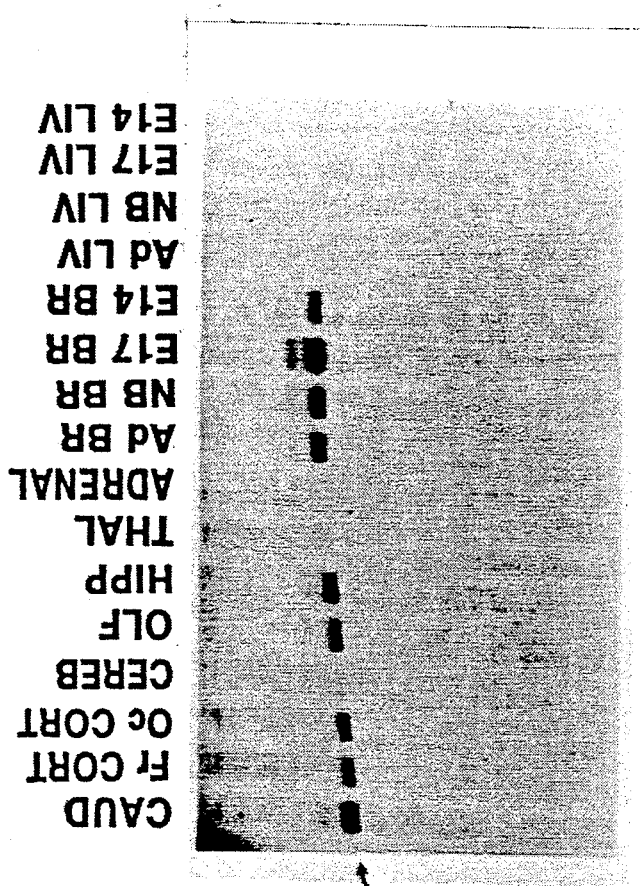
FIGS. 4A and 4B Ribonuclease protection assays of total RNA from rat tissues. A 309 nucleotide fragment is specifically protected by the BF-1 mRNA. A) The protected band is detectable only in the brain. M-molecular weight markers; I-small intestine; L-liver; B-brain; S-spleen; K-kidney; T-testis. B) RNA prepared from different regions of the adult brain, adrenal gland, and whole brain or liver from four different stages of development. CAUD-caudate putamen; Fr CORTfrontal cortex; OC CORT-occipital cortex; CEREB-cerebellum; OLF-olfactory bulb; HIPP-hippocampus; THAL-thalamus; Ad-Adult; NB-newborn; E17-embryonic day 17; E14-embryonic day 14; BR-brain; LIV-liver.
Figure 4A:
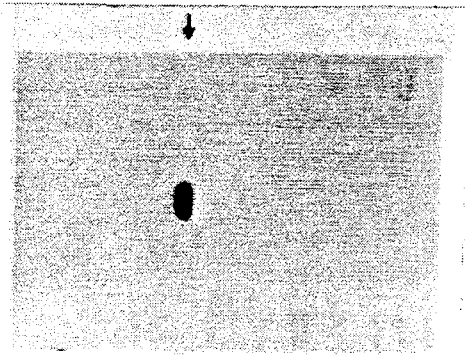

We examined the expression pattern of BF-1 initially by Northern analysis of poly A+ RNA isolated from both adult and fetal rat tissues. FIG. 3 shows that a 2.9 kB mRNA species is present in samples isolated from total brain using a probe derived from the BF-1 cDNA which does not contain the DNA binding domain. No expression is apparent in the lung, liver, and intestine (FIG. 3). The quantity of RNA in each lane is assessed by hybridization of the filter with a probe for GAPDH, which is found in similar abundance in all tissues. The Northern analysis was confirmed with RNase protection assays using a probe corresponding to nucleotides 1140-1449 of the cDNA. FIG. 4A shows the presence of the specifically protected probe of 309 nucleotides with total RNA from brain but not from liver, kidney, spleen and intestine. The quantity of the RNA was assessed to be equivalent among all the samples used in these assays by staining after electrophoresis in an agarose gel to visualize the 18S and 28S rRNA bands.

Levels of Expression of BF-1 in the Developing Rat Brain

Northern analysis showed that the mRNA was several-fold more abundant in embryonic day 17 (E17) brain than in the adult brain (FIG. 3). Additional studies which allowed better quantitation were performed with RNase protection assays on RNA from tissue during fetal development. FIG. 4 shows that BF-1 expression is detectable in E14 brain, increases to peak levels by day 17 and declines thereafter to adult levels. The data show that BF-1 is four-fold more abundant in E17 brain compared to the adult brain. Fetal and adult liver RNA were also assayed and not found to express BF-1 at any stage of development. We used total RNA isolated from dissected regions of the adult rate brain to study the regional distribution of BF-1 expression in RNAse protection assays. FIG. 4B reveals the BF-1 is expressed in the cortex, olfactory bulb, hippocampus and in the caudate putamen. Expression is absent in the cerebellum and thalamus. Adrenal tissue also does not express BF-1. The amount of RNA in each sample was verified to be the same in a Northern blot using a probe to 18S RNA (Ehrlich et al. 1990).

Expression of BF-1 is Restricted to the Telencephalon of the Developing Brain

Examination of rat brain sections by in situ hybridization, confirmed the region restricted expression pattern of BF-1. FIGS. 5J and 5K are autoradiographs of sections of adult brain hybridized with an antisense probe for BF-1. The cerebral cortex, caudate putamen, hippocampus and dentate gyrus show levels of BF-1 expression significantly above background while the thalamus, cerebellum and brainstem do not. This restricted expression to telencephalon-derived structures is even more clearly seen in the E17 brain. FIG. 5E shows a brightfield view of a parasagittal brain section. The autoradiograph of this section (FIG. 5F) and two coronal sections (FIG. 5G and H) shows high level expression in the cerebral cortex and caudate putamen and no significant expression in the more caudal regions of the brain. The specificity of this signal for BF-1 is shown in FIG. 5I, an autoradiograph of a section parallel to that shown in 5E, hybridized with a sense probe to BF-1. This restriction of BF-1 expression is established early in development. FIG. 5A-D show that BF-1 expression is limited in the nervous system to the most rostral region of the developing brain. We detect high levels of BF-1 mRNA in the ventricular zone surrounding the lateral ventricles at E11.5 soon after the telencephalic evaginations arise (Rugh 1968). The level of expression declines between E17 and the adult (FIG. 5J, K), consistent with the results obtained with analysis of whole brain RNA. The autoradiographs for the embryonic sections are exposed for one-third of the time as the adult sections. Thus expression levels per cell falls about 10-20 fold.

Figure 6A:
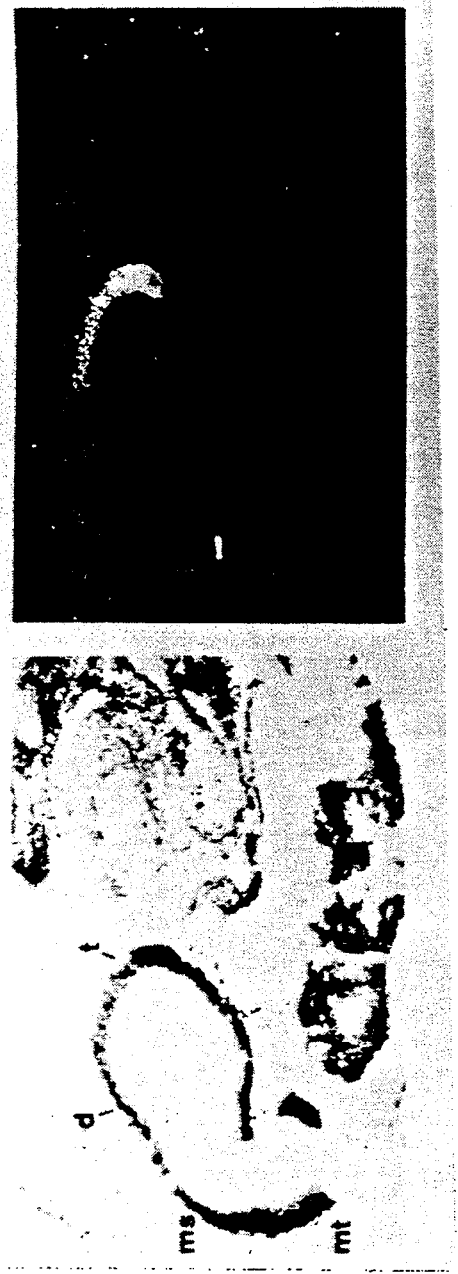
FIGS. 6A–6C Restriction of BF-1 expression to the telecephalon of the developing brain. Brightfield and darkfield photomicrographs of sections hybridized with a BF-1 antisense probe. A) Sagittal section from E10 with hybridization signal over the rostral end of the neural tube. B) Parasagittal section from E10 again with signal over the rostral neural tube as well as the auditory vesicle and pharyngeal pouches. C) Transverse section from E11.5 caudal to the section shown in FIG. 5A. t, telencephalon; d, diencephalon; ms, mesencephalon; av, auditory vesicle; php, pharyngeal pouches; olf, olfactory placode; r, retinal neuroepithelium; sb, superior bridge.
Figure 6B:
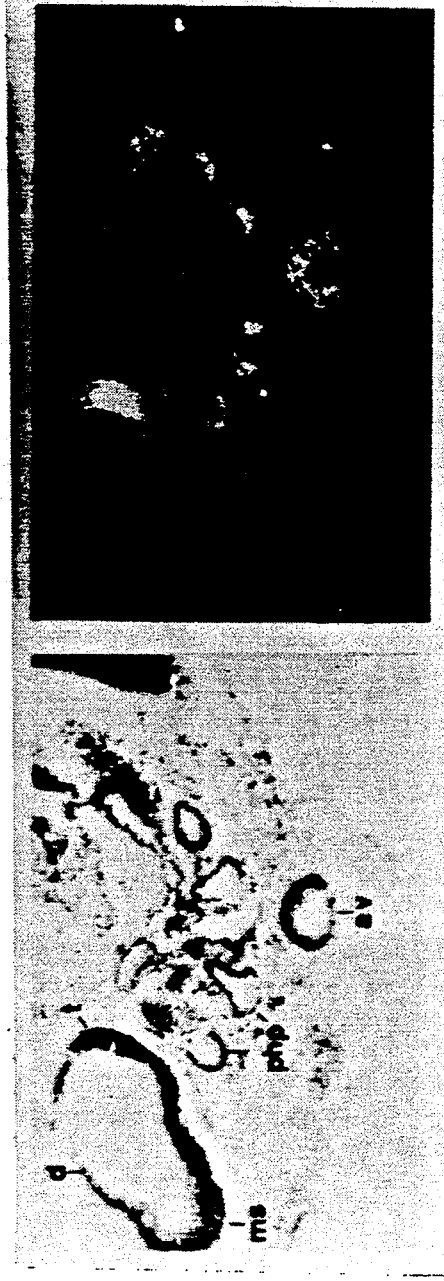
Figure 6C:
Figure 7A:
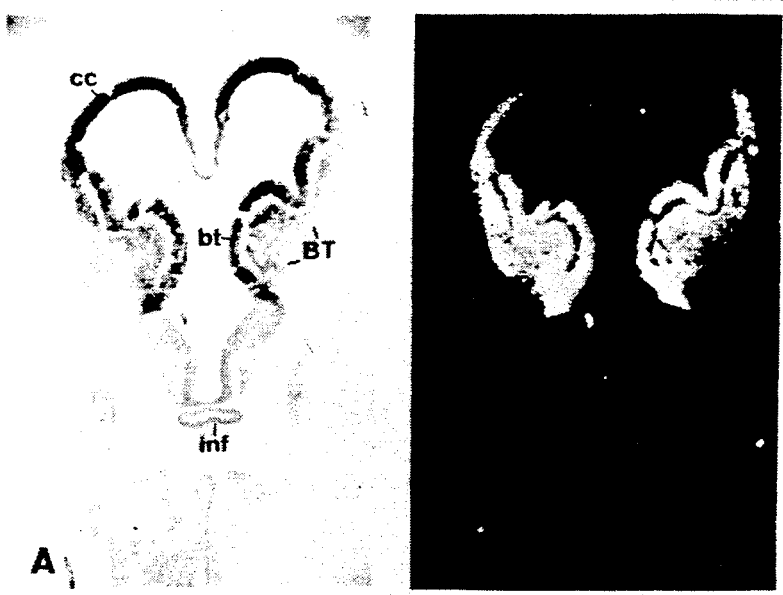
FIGS. 7A and 7B Restriction of BF-1expression to the telencephalon at embryonic day 13.5. Brightfield and darkfield photomicrographs of sections hybridized with a BF-1 antisense probe. A) Transverse section from E13.5 with hybridization signal over the cerebral cortical neuroepithelium, the basal telencephalon neuroephithelium and the differentiating basal telencephalon. B) Transverse section rostral to that in A with hybridization over the cerebral cortical neuroepithelium. No detectable signal over the thalmic and hypothalmic neuroepithelium. cc, Cerebral cortical neuroepithelium; bt, basal telencephalic neuroepithelium; BT, basal telencephalon(differentiating); inf, infundibulum; th, thalamus; hy, hypothalamus; my, myelencephalon; lv, lateral ventricle; v3, third ventricle.
Figure 7B:
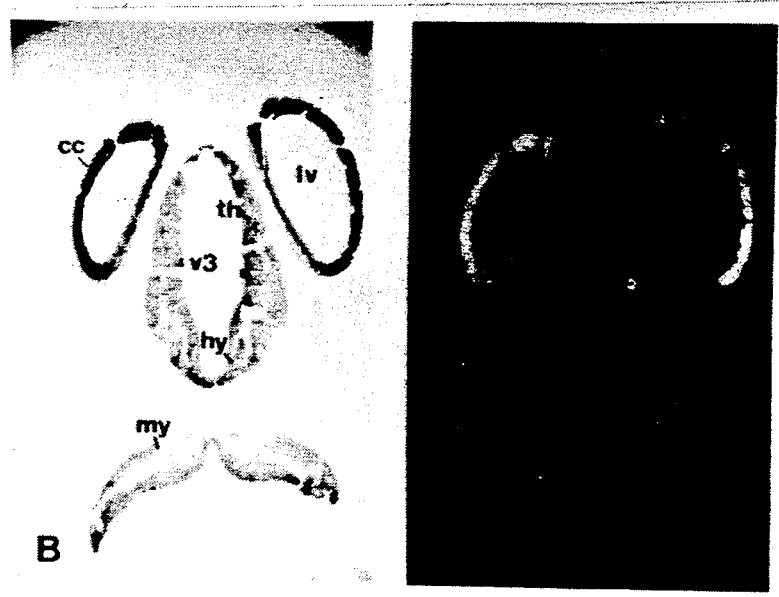

Higher magnification views show more clearly the restriction of expression within the developing forebrain to the telencephalon. High level of BF-1 are detectable in the rostral neuroepithelium of E10 embryos, shown in matching brightfield and darkfield views (FIG. 6A and 6B). At this stage, it is difficult to distinguish the border between the telencephalic and diencephalic neuroepithelium. The rapid proliferation of the cells of the telencephalon results in distinct telencephalic vesicles by E11.5 (FIG. 6C). Here we observe high levels of BF-1 expression in the neuroepithelium surrounding the lateral ventricles. By contrast, structures of the diencephalic neuroepithelium, including the optic stalk and the optic sup which will develop into the retina, are clearly devoid of BF-1 (FIG. 6C, 5A, 5B). In order to further demonstrate the restriction of BF-1 expression to the telencephalic neuroepithelium and the structures arising from it, we show two additional view of the telencephalon and diencephalon from E13.5 in FIG. 7. At this stage, the earlier onset of neurogenesis in the basal telencephalon is apparent by the presence of larger differentiating fields around the basal telencephalic neuroepithelium, compared with the cerebral cortical neuroepithelium (FIG. 7A). The differentiating cells of the basal telencephalon express BF-1 at least as highly as the neuroepithelium. Expression of BF-1 abruptly terminates caudal to this region. An adjacent section further shows the absence of expression in the diencephalon and also shows absence of expression in the medial wall of the telencephalic vesicles (FIG. 7B). This region of the telencephalic neuroepithelium expresses BF-1 earlier in development but begins to decrease expression with the infolding of the superior bridge and the establishment of the telencephalic vesicles (FIG. 6C).

A few localized sites of expression are detected outside of the central nervous system, including the olfactory placode which gives rise to the nasal epithelium (FIG. 6C), the auditory vesicle and the pharyngeal pouches (FIG. 6B). Expression at these sites declines through embryogenesis. The absence of expression through development in the tissues where HNF-3 proteins are expressed, the liver, the lung and the intestine are confirmed by in-situ data (FIG. 5A-D).

BF-1 Shares Homology With the HNF-3 Family in the DNA Binding Domain

Comparison of the sequence of BF-1 with the members of the HNF-3 family shows that it contains a homologous region from amino acids 162-271 corresponding to the DNA binding domain previously identified in the HNF-3 family (FIG. 1 (SEQ. ID. No. 2)). However, whereas the HNF-3 family members are 85% identical within the entire 110 amino acid region, BF-1 is considerably more divergent. This divergence is greater than that of the Drosophila fork head gene from the rat HNF-3 genes. Thus, fork head is the Drosophila homolog of HNF-3a, 3b, and 3g, while BF-1 is in a distinct subfamily. The homology is not uniform within this domain. It is apparent that the central portion with 74% of the amino acids (32/43 aa) identical comprises the most highly conserved structure while the carboxyl third of this region is only 36% identical (13/36 aa). FIG. 1 (SEQ. ID. NO. 2) shows the amino acids in the DNA binding domain which are identical to at least two of the other four members of the HNF-3/fork head family. These differences raised the likelihood that BF-1, if it bound to DNA, might have a distinct binding specificity. The sequence of BF-1 is notable for several other features. First, it does not share the two other conserved short domains II and III carboxyl to the binding domain which are found in the HNF-3 and fork head genes (Lai, Prezioso et al. 1991). However, a short sequence similar to that in domain II is present in the amino terminal end of BF-1 (amino acids 18-24, FIG. 1 (SEQ. ID. NO. 2)). The function of these domains remains unknown. Finally, BF-1 contains proline and glutamine rich regions, which have previously been shown in other transcription factors to confer activation function (Courey and Tjian 1988; Mermod et al. 1989).

BF-1 is a Sequence Specific DNA Binding Protein With a Distinct Binding Specificity Because of the differences in the amino acid sequence in the binding domain as compared with HNF-3 proteins, we were not surprised to find that BF-1 did not bind readily to the strong HNF-3 site from the transthyretin (TTR) promoter.

Figure 8:
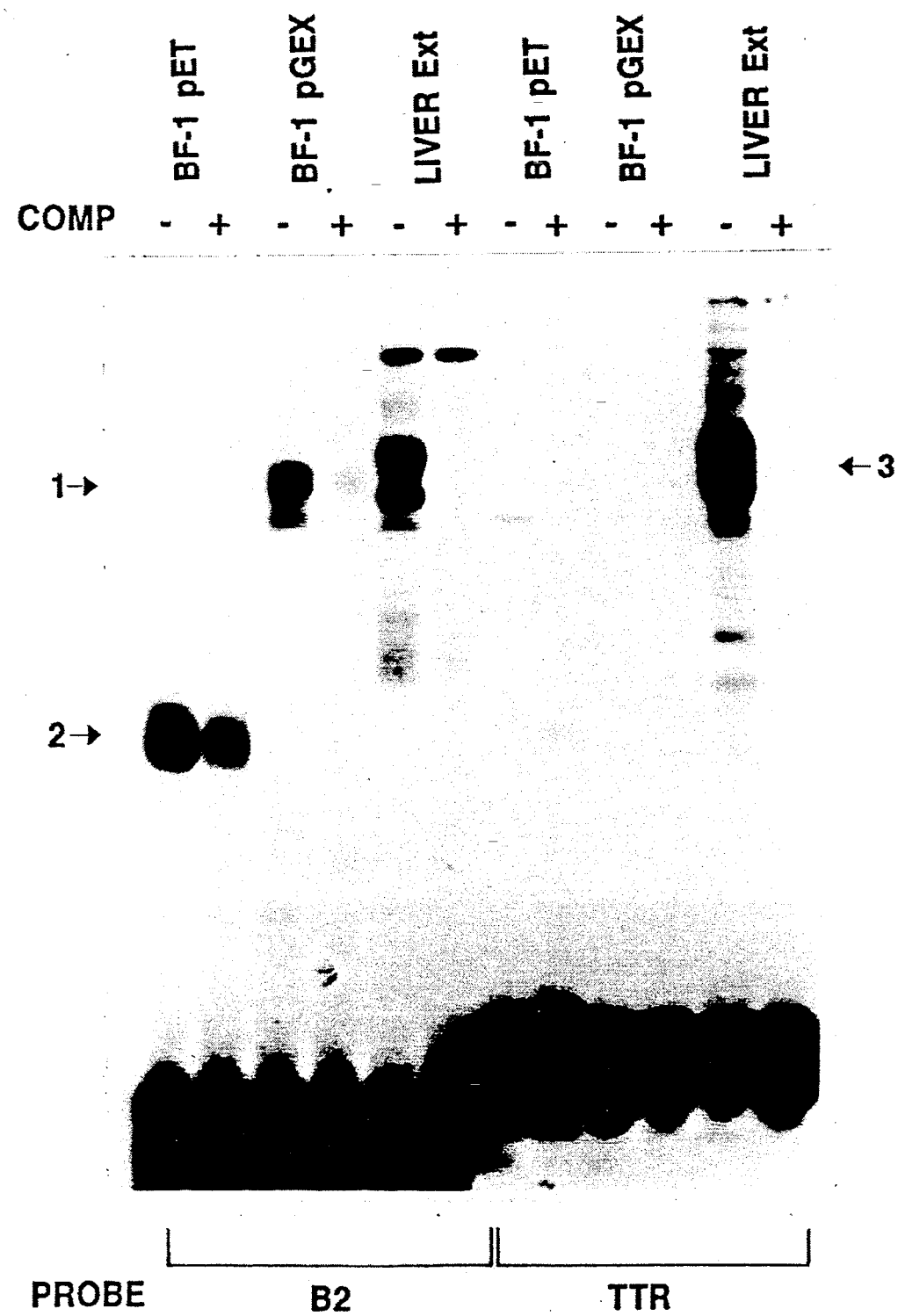
FIG. 8 Sequence specific binding of BF-1. Autoradiograph of a gel mobility shift assay comparing two BF-1 fusion proteins and liver extract using two different labeled probes, B2 site from the HNF-1 promoter and TTR from the transthyretin promoter. 1) BF-1 pGEX-DNA complex with the B2 probe, 2) BF-1 pET-DNA complex with the B2 probe, 3) the three complexes in liver extract from HNF-3a, 3b and 3g with both B2 and TTR probes. Alternate lanes include (−) no competitor or (+) 40-fold molar excess of unlabeled homologous competitor.

This site has been previously shown to be located between nucleotides −58 and −111, upstream of the transcription initiation site (Costa et al. 1989). However, when we used a large amount of bacterially expressed fusion protein (25 ng) which contained the binding domain of BF-1, we were able to detect a weak complex in gel mobility shift experiments using this probe. This suggested that BF-1 was a DNA binding protein with a low affinity for this site. We reasoned that a preferred binding site would have some similarity to the site in the TTR promoter, so we obtained and tested a series of oligonucleotides which contained different sites which bind to the HNF-3 proteins. We compared two bacterially produced fusion proteins containing 206 amino acids of the BF-1 protein in gel mobility shift assays with HNF-3 proteins from a liver extract. Interestingly, we found one HNF-3 site from the promoter of the HNF-1a gene called B2 (Kuo et al. 1992) which binds to BF-1 with at least twenty-fold greater affinity than any of four other sites tested. FIG. 8 shows a gel mobility shift experiment using two different probes, the TTR promoter site and the B2 site. Whereas liver nuclear extract (containing at least three HNF-3 proteins) binds to the TTR site with a slightly higher affinity compared to the B2 site, both BF-1 fusion proteins have a markedly greater affinity for the B2 site compared to the TTR site. One fusion protein using the pET vector adds 14 aa to the amino terminal end (Rosenberg et al. 1987) while the other using the pGEX vector adds 27.5 kD of glutathione transferase to the amino terminal end (Smith and Johnson 1988). These 206 amino acids of BF-1 contain the entire DNA binding domain as determined by sequence homology with the HNF-3 proteins. It has been determined for HNF-3 proteins that the binding domain alone has DNA binding properties indistinguishable from the intact protein (Tao and Lai, unpublished data). BF-1 also did not bind to three other HNF-3 sites from the a-1 antitrypsin gene, a second site from the transthyretin gene (Costa, Grayson et al. 1989), and the albumin gene (Liu et al. 1991). These results show that BF-1 has distinct DNA binding specificity from that of the HNF-3 proteins. The identical DNA binding properties of two different BF-1 fusion proteins indicate that DNA biding is attributable to the BF-1 portion of the protein. However, The affinity of BF-1 for the B2 site is relatively low compared to the affinity of the HNF-3 proteins for this site. Studies are in process to identify the optimal recognition sequences for this protein.

Discussion

We have cloned and characterized, BF-1, a new member of the HNF-3 family from a rat brain cDNA library. BF-1 shares homology in the DNA binding domain with HNF-3a, 3b, 3g and Fork head but clearly belongs to a different subfamily based on significant divergence in the carboxyl third of this domain. This divergence in sequence likely reflects some differences in function as underscored by our findings that BF-1 is expressed in a completely distinct pattern than the HNF-3 proteins and the BF-1 has a different DNA binding specificity. Consistent with a role in central nervous system development, BF-1 is expressed at high levels in specific regions of the brain during embryogenesis. These results suggest that an extended family of transcription factors related to the HNF-3 proteins exists which have a broader role in mammalian development than previously believed. Members of the extended HNF-3 family are not only expressed in gut endoderm derived tissues but in the central nervous system as well. The emerging picture is that of a large gene family with distinct subfamilies of transcription factors, each of which may regulate the development of distinct subsets of tissues. The brain-specific subfamily comprises BF-1 and at least two additional members. An additional member of this family which is present in lymphoid cells has recently been reported (Li et al. 1991).

The restricted expression of BF-1 to the telencephalon at early stages in brain development suggests that it plays a role in the regional differentiation of the neural tube. It has been suggested that signals from the underlying mesoderm during gastrulation lead to the commitment of different regions of the neural tube to form different parts of the central nervous system. The forebrain forms above the prechordal plate (Bergquist and Kallen 1954), rather than the notochord and floor plate which has been shown to provide inductive signals to the spinal cord (Placzek, Tessier-Lavigne et al. 1990; Yamada et al. 1991). Thus, it would be expected that different signals are received in this region of the neural tube, resulting in distinct patterns of gene expression.

The forebrain subsequently subdivides into the telencephalon and the diencephalon. The restricted expression of BF-1 to the rostral portion of the forebrain prior to its morphologically apparent subdivision into two vesicles and its structural homology to fork head, a putative transcriptional regulator, suggests that it is likely to be an important intermediary in the regulatory cascade which commits the cells of the rostral neural tube to the formation of the telencephalon. The fork head mutation causes a homeotic transformation of the terminal regions of the embryo. Foregut and hindgut are replaced by ectopic head structures (Jurgens and Weigel 1988). BF-1 expression is first evident in the proliferating neuroepithelial precursor cells surrounding the telocoel. As development progresses, these cells differentiate into neuronal and glial cells and migrate outward. The expression of BF-1 persists in the postmitotic cells and by E17 is uniformly detected in the telencephalic structures. Expression is clearly evident in neurons as exemplified by the in-situ signals of the hippocampus and dentate gyrus (FIG. 5K). Expression in the adult is restricted to the gray matter and the large increase in BF-1 expression between E14 and E17 correlates well with the period of rapid neuronal proliferation. Furthermore, expression of BF-1 per cell in the cerebral hemispheres declines postnatally, correlating with the major period of glial proliferation. These results suggest that BF-1 is primarily expressed in neurons but we cannot exclude expression in glia. The relative uniformity of expression in the cerebral cortex and the caudate putamen indicates that BF-1 does not primarily direct the final differentiation of the many neuronal phenotypes found in these parts of the brain. Rather, BF-1 appears to function at an earlier step in the differentiation pathway to commit the precursor cells to form specific regions of the brain and not specific cell types. Its restriction to the rostral end of the neural tube is reminiscent of the restriction of fork head to the anterior and posterior termini of the early Drosophila embryo. Thus we postulate that BF-1 functions in regional specialization of the central nervous system in a manner analogous to the function of fork head in the regional specialization of the terminal structures in Drosophila.

Other putative transcriptional regulators have been found to be restricted to specific regions of the developing brain, including several homeodomain proteins and one zinc finger protein in specific rhombomers of the hindbrain (Murphy, Davidson et al. 1989; Wilkinson, Bhatt et al. 1989; Wilkinson, Bhatt et al. 1989; Kesseland Gruss 1990; He and Rosenfeld 1991). Only a few examples of region-specific expression exist for the other regions of the brain. En-2 is expressed at the midbrain and hindbrain junction (Davis and Joyner 1988; Davis et al. 1988) and recently, two genes related to Distal-less were found to be expressed in a restricted pattern within the forebrain. Tes-1 and Dlx are expressed in the ventral forebrain of the mid-gestation embryo, in both the telencephalon and diencephalon (Porteus et al. 1991; Price et al. 1991). These factors along with BF-1 are likely to be part of the molecular basis of the regional organization of the developing neural tube. Still other transcription factors such as several members of the POU-domain family which are expressed in specific patterns in the developing brain but are not restricted to any single region (He et al. 1989), may function to determine specific phenotypes such as the different types of neurons and glia. The function of BF-1 in the adult brain is not readily apparent but may be related to maintaining the expression of those genes which are common to telencephalon derived structures. The product of one such gene has been detected as a telencephalon specific antigen in the rabbit (Mori et al. 1987) This antigen is restricted to the gray matter of the cerebral hemispheres and increases postnatally from low levels at birth.

Experimental Procedures

Isolation and Sequencing of cDNA Clones of Rat and Murine BF-1

The rat BF-1 cDNA was obtained by screening a lgt11 library from whole adult rat brain generously provided by Dr. Streamsen Chua, using a random hexamer primed probe spanning nucleotides 596-923 of the of the HNF-3a cDNA. This probe contains the region encoding the DNA binding domain. Hybridization and washes were performed as previously described except for hybridization at 50° C. and the final wash at 50° C. in 2X SSPE. From 500,000 recombinants, 10 positive clones were analyzed further. Six of these proved to be overlapping clones of a single cDNA as determined by restriction mapping and partial sequence. The largest clone was used for subsequent studies.

Sequencing was performed by the dideoxy chain termination method on double stranded templates. The sequence was determined completely on both strands with overlapping subcloned and exonuclease shortened templates, and for nucleotides 1-2000 also with ITP-containing sequencing mixes (United States Biochemicals Sequenase kit) to eliminate compression artifacts.

Northern and Ribonuclease Protection Analyses

RNA was isolated from rat tissues by the acid guanidinium thiocyanate-phenol-chloroform extraction method (Chomczynski and Sacchi 1987; Puissant Houdebine 1990). Pregnant Sprague-Dawley rats were obtained from Harlan Sprague Dawley, timed at embryonic day 0.5 on the morning following an evening mating. Poly(A)+ RNA was selected by chromatography on oligo(dT) cellulose. Northern analyses with 2 mg poly-A+ RNA were performed as previously described.

Ribonuclease protection assays were performed with 10 mg total RNA as described previously (Costa et al. 1986), RNA probes were synthesized from a pBluescript plasmid containing the fragment of the BF-1 cDNA from neucleotides 1140-1449, linearized with PvuII, using T7 polymerase. The probe is 457 nucleotides in length and the protected fragment is 309 nucleotides. Samples were analyzed on 6% acrylamide-urea gels which were dried and exposed to X-ray film with screen for 16-48 hrs.

In-situ Hybridization

Brain tissue was obtained from adult male Sprague-Dawley rats perfused with 4% paraformaldehyde or rat embryos. 8 micron paraffin sections were dewaxed in xylene and then processed essentially as described previously (Kuo et al. 1988). S-35 labeled riboprobes were synthesize using T7 (antisense) or T3 (sense) RNA polymerase from linearized plasmid templates containing the BF-1 cDNA from the Nhe I site at nucleotide 1265 to 3' end (SEQ. ID. NO. 1). This probe does not contain the sequence encoding the DNA binding domain. Hybridization was for 16 hrs at 58° C. and the high stringency washes were performed at 60° C. in 2X SSC/50% formamide. Embryonic tissue sections were exposed to film for 16 hrs and to NTB-2 emulsion for 48 hrs. Adult sections were exposed for 48 hrs and 6 days respectively.

Fusion Proteins and Gel Mobility Shift Assays

The fragment of the rat BF-1 cDNA from nucleotides 785 to 2240 (SEQ. ID. NO. 1) was cloned into the BamH1 site of the pGEX-3X vector (Pharmacia) which yields a protein with 27.5 K of glutathione transferase fused to 206 amino acids of BF-1 containing the DNA binding domain. The protein was expressed in *E. coli* SF8 cells. The fusion protein was purified from the crude bacterial extract by adsorption of glutathione agarose beads followed by elution with glutathione (Smith and Johnson 1988). The quantity of the partially purified protein used in binding assays was determined by Coomassie Blue staining. A second expression plasmid was constructed by ligating this fragment of BF-1 into the BamHI site of the pET-3c vector which yields a protein of 14 amino acids fused to 206 amino acids of BF-1. The crude lysate from bacteria expressing this fusion protein were used directly in binding assays (Studier and Moffatt 1986). 5 $\mu$g of BF-1 pET bacterial lysate, 25 ng of BF-1 pGEX, or 5 $\mu$g of liver nuclear extract was incubated with either B2 or TTR oligonucleotide probe as described previously (Lai, Prezioso et al. 1990).

The sequence of the binding site oligonucleotide from the transthyretin (TTR) promoter and the gel mobility shift assay have been described previously. The sequence of the binding site oligonucleotide from the HNF-1 promoter (B2) has also been described (Kuo, Conley et al. 1992).

References

Bergquist, H. and B. Kallen (1954). Notes on the early histogenesis and morphogenesis of the central nervous system in vertebrates, J. Comp. Neurol. 100: 627–659.

Chomczynski, P. and N. Sacchi (1987). Single-step method of RNA isolation by acid guanidinium thiocyante-phenol-chloroform extraction. Anal. Biochem. 162: 156–159.

Costa, R. H. D. R. Grayson and J. E. Darnell Jr (1989). Multiple hepatocyte-specific nuclear factors function in the regulation of the transthyretin and a1-antitrypsin genes. Mol. Cell Biol. 9: 1415–1425.

Costa, R. H., E. Lai and J. E. Darnell Jr (1986). Transcriptional control of the mouse prealbumin (transthyretin) gene: Both promoter sequences and a distinct enhancer are cell specific. Mol. Cell Biol. 6: 4697–4708.

Courey, A. and R. Tjian (1988). Analysis of Sp1 in vivo reveals multiple transcriptional domains, including a novel glutamine-rich activation motif. Cell 55: 887–898.

Davis, C. A. and A. L. Joyner (1988). Expression patterns of the homeo box-containing genes En-1 and En-2 and the proto-oncogene int-1 diverge during mouse development. Genes & Dev. 2: 1736–1744.

Davis, C. A., S. E. Noble-Topham, J. Rossant and A. L. Joyner (1988). Expression of the homeo-box containing gene En-2 delineates a specific region of the developing mouse brain. Genes & Dev. 2: 361–371.

Duboule, D. and P. Dolle (1989). The murine Hox gene network: its structural and functional organization resembles that of the Drosophila homeotic genes. EMBO J. 8: 1497–1505.

Ehrlich, M. E. T. Kurihara and P. Geengard (1990). Rat DARPP-32: Cloning, sequencing and characterization of cDNA. J. Mol. Neurosci. 2: 1–10.

Graham, A., N. Papalopulu and Krumlauf (1989). The murine and Drosophila hemeobox gene complexes have common features of organization and expression. Cell 57: 367–378.

He, X. and M. G. Rosenfeld (1991). Mechanisms of complex transcriptional regulation: implications for brain development, Neuron 7: 183–196.

He, X., M. Treacy, D. Simmons, et al. (1989). Expression of a large family of POU-domain regulatory genes in mammalian brain development. Nature 340: 35–42.

Hunt, P., M. Gulisano, M. Cook, et al. (1991). A distinct Hox code for the branchial region of the vertebrate head. Nature 353: 861–864.

Jurgens, G. and D. Weigel (1988). Terminal versus segmental development in the Drosophila embryo: the role of the homeotic gene fork head. Roux's Arch. Dev. Biol. 197: 345–354.

Kandel, E., J. H. Schwartz and T. M. Jessell (1991). Principles of Neural Science. New York, Elsevier.

Kessel, M. and P. Gruss (1990). Murine developmental control genes. Science 249: 374–379.

Kozak, M. (1986). Point mutations define a sequence flanking the AUG initiator codon that modulates translation by eukaryotic ribosomes. Cell 44: 283–292.

Kuo, C. F., K. E. Paulson and J. E. Darnell Jr (1988). Positional and developmental regulation of glutamine synthetase expression in mouse liver. Mol. Cell Biol. 8: 4966–4971.

Kuo, C. J., P. B. Conley, L. Chen, et al. (1992). A transcriptional hierarchy involved in mammalian cell-type specification. Nature 355: 457–461.

Lai, E., V. R. Prezioso, E. Smith, et al. (1990). HNF-3A, A hepatocyte-enriched transcription factor of novel structure is regulated transcriptionally. Genes & Dev. 4: 1427–1436.

Lai, E. V. R. Prezioso, W. Tao, W. S. Chen and J. E. Darnell Jr. (1991). Heptacyte nuclear factor 3a belongs to a gene family in mammals that is homologous to the Drosophila homeotic gene fork head. Genes & Dev. 5: 416–427.

Li, C., C. Lai, D. S. Sigman and R. B. Gaynor (1991). Cloning of a cellular factor, interleukin binding factor, that binds to NFAT-like motifs in the human immunodeficiency virus long terminal repeat. Proc. Natl. Acad. Sci. USA 88: 7739–7743.

Liu, J. K., C. M. DiPersio and K. S. Zaret (1991). Extracellular signals that regulate liver transcription factors during hepatic differentiation in vivo. Mol. Cell Biol. 11: 773–784.

Mangold, O. (1933). Uber die induktions fahigkeit der verschiederen Bezirke der Neurule von Vrodelen. Naturwissenschafer 21: 761–766.

McKay, R. D. G. (1989). The origins of cellular diversity in the mammalian central nervous system. Cell 48: 815–821.

Mermod, N., E. O'Neill, T. Kelly and R. Tjian (1989). The proline-rich transcriptional activator of CTF/NF-1, is distinct from the replication and DNA binding domain. Cell 58: 741–753.

Mori, K., S. C. Fujita, Y. Watanabe, K. Obata and O. Hayaishi (1987). Telenephalon-specific antigen identified by monoclonal antibody. Proc. Natl. Acad. Sci. USA 84: 3921–3925.

Murphy, P., D. R. Davidson and R. E. Hill (1989). Segment-specific expression of a homeobox-containing gene in the mouse hindbrain. Nature 341: 156–159.

Placzek. M., M. Tessier-Lavigne, T. Yamada, T. Jessell and J. Dodd (1990). Mesodermal control of neural cell identity: floor plate induction by the notochord. Science 250: 985–987.

Porteus, M., A. Bulfone, R. Ciaranello and J. Rubenstein (1991). Isolation and characterization of a novel cDNA clone encoding a homeodomain that is developmentally regulated in the ventral forebrain. Neuron 7: 221–229.

Price, M., M. Lemaistre, M. Pischetola, R. DiLauro and D. Duboule (1991). A mouse gene related to Distal-less shows a restricted expression in the developing forebrain. Nature 351: 748–751.

Puissant, C. and L. Houdebine (1990). An improvement of the single-step method of RNA isolation by acid guanidinium thiocyanate-phenol-chloroform extraction. BioTechniques 8: 148–149.

Rosenberg, A. H., B. N. Lade, D. Chui, et al. (1987). Vectors for selective expression of cloned cDNAs by T7 RNA polymerase. Gene 56: 125–135.

Rugh, R. (1968). The mouse: its reproduction and development. New York, Oxford University Press.

Smith, D. B. and K. S. Johnson (1988). Single-step purification of polypeptides expressed in *E. coli* as fusions with glutathione S-transferase. Gene 67: 31–40.

Spemann, H. (1938). Embryonic development and induction. New Haven, Yale Univ. Press.

Studier, F. W. and B. A. Moffatt (1986). Use of bacteriophage T7 RNA polymerase to direct selective high-level expression of cloned genes. J. Mol. Biol. 189: 113–130.

Weigel, D. and H. Jackle (1990). Fork head: A new eukaryotic DNA binding motif? Cell 63: 455–456.

Weigel, D., G. Jurgens, F. Kuttner, E. Seifert and H. Hackle (1989). The homeotic gene fork head encodes a nuclear protein and is expressed in the terminal regions of the Drosophila embryo. Cell 57: 645–658.

Wilkinson, D. G., S. Bhatt, P. Chavrier, R. Bravo and P. Charnay (1989). Segment-specific expression of zinc-finger gene in the developing nervous system of the mouse. Nature 337: 461–464.

Wilkinson, D. G., S. Bhatt, M. Cook, E. Boncinelli and R. Krumlauf (1989). Segmental expression of Hox-2 homeobox-containing genes in the developing mouse hindbrain. Nature 341: 405–409.

Yamada, T., M. Placzek, H. Tanaka, J. Dodd and T. J. Jessell (1991). Control of cell pattern in the developing nervous system: polarizing activity of the floor plate and notochord. Cell 64: 635–647.

---

What is claimed is:

1. An isolated nucleic acid molecule encoding the transcription factor BF-1.

2. The isolated nucleic acid molecule of claim 1, wherein the nucleic acid molecule is a messenger RNA molecule.

3. The isolated nucleic acid molecule of claim 1, wherein the nucleic acid molecule is a DNA molecule.

4. The DNA molecule of claim 3, wherein the DNA molecule is a genomic DNA molecule.

5. The DNA molecule of claim 3, wherein the DNA molecule is a cDNA molecule.

6. The cDNA molecule of claim 5 having a nucleotide sequence shown in FIG. 1-1 through 1-3 (SEQ ID No. 1).

7. The cDNA molecule of claim 5 labelled with a detectable marker.

8. An expression vector comprising the isolated DNA molecule of claim 5 operably linked to a RNA polymerase promoter.

9. A method of producing a transcription factor expressed in the telencephalic region of the brain of a developing vertebrate animal or in structure derived therefrom, which comprises growing a host vector system comprising an expression vector having the isolated DNA molecule of claim 5 operably linked to a RNA polymerase promoter under conditions which permit transcription and translation, followed by recovering the transcription factor so produced.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 2830 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: N ( i v ) ANTI-SENSE: N ( i x ) FEATURE:
        ( A ) NAME/KEY: CDS
        ( B ) LOCATION: 443..1882
        ( D ) OTHER INFORMATION:

( i x ) FEATURE:
        ( A ) NAME/KEY: miscfeature
        ( B ) LOCATION: 926..1255
        ( D ) OTHER INFORMATION: /note="nucleotide sequence encoding DN binding domain homology"

( i x ) FEATURE:
        ( A ) NAME/KEY: miscsignal
        ( B ) LOCATION: 1883..1885
        ( D ) OTHER INFORMATION: /note="translation termination codon"

( x i ) SEQUENCE DESCRIPTION: SEQ ID NO:1:

```
GGCGGCCGCT CCGGGACGCG CCCGCGCGCT GCCCGGCTCT CCCCCCCTTC GGGCTGCCGC        60

TGCTGCTGCT GTGACTGCTG CGGCGCGAGG AGGAGGAGGC AGCGGGGGAG GGGGAGGCCG       120

GGCGCGGAAC GGAGCGGGGC GCTGCACCCC GGGCGACGGG TTGCTTCTGC CTCTAGCTTC       180

TCTCTCTCTC TCTCTCTCTC TCTCTCTCTC TCTCTCTCTC TCTCTCTCTC TCTCTCTCTC       240

TAATTCTTGA GGGGTGGTTG CAGCTTTTGC TACATGCCTT GCCAGCGCCG GAGCCTGCGG       300
```

-continued

| | | | | |
|---|---|---|---|---|
| TCCAACTGCG | CTGCTGCCGG | AGCGCTCAGT | GCCGCCCCCG | CTGCCCGCTC CCCCCGCTCC | 360 |
| CCACTCCGAA | CCCGCCGGTC | GCTCGCCGCG | CTGCTGCTCG | GCTCCTGCGC CGCCGCCGTC | 420 |
| GCCCCCCCCC | GACGCCTGGG | TG ATG CTG | GAC ATG GGA | GAT AGG AAA GAG GTG | 472 |

Met Leu Asp Met Gly Asp Arg Lys Glu Val
                                             1              5                    10

| | | | | | | | | | | | | | | | |
|---|---|---|---|---|---|---|---|---|---|---|---|---|---|---|---|
| AAA | ATG | ATT | CCC | AAG | TCC | TCG | TTC | AGC | ATC | AAC | AGC | CTG | GTC | CCT GAG | 520 |
| Lys | Met | Ile | Pro | Lys | Ser | Ser | Phe | Ser | Ile | Asn | Ser | Leu | Val | Pro Glu | |
| | | | | 15 | | | | | 20 | | | | | 25 | |
| GCC | GTC | CAG | AAC | GAC | AAC | CAC | CAC | GCG | AGC | CAC | GGC | TAC | CAC | AAC AGC | 568 |
| Ala | Val | Gln | Asn | Asp | Asn | His | His | Ala | Ser | His | Gly | Tyr | His | Asn Ser | |
| | | | 30 | | | | | 35 | | | | | 40 | | |
| CAC | CAC | CCC | CAG | CAT | CAC | CAT | CAT | CAC | CAC | CAC | CAC | CAC | CCG | CCG | 616 |
| His | His | Pro | Gln | His | His | His | His | His | His | His | His | His | Pro | Pro | |
| | | | 45 | | | | | 50 | | | | | 55 | | |
| CCG | CCC | GCG | CCT | CAG | CCG | CCG | CCA | CCG | CCG | CAG | CAG | CAG | CAG | CAG | 664 |
| Pro | Pro | Ala | Pro | Gln | Pro | Pro | Pro | Pro | Pro | Gln | Gln | Gln | Gln | Gln | |
| | | 60 | | | | | 65 | | | | | 70 | | | |
| CCG | CCC | CCG | GCC | CCG | CAG | CCC | CCG | CAG | GCG | CGC | GGC | GCC | CCA | GCA GCG | 712 |
| Pro | Pro | Pro | Ala | Pro | Gln | Pro | Pro | Gln | Ala | Arg | Gly | Ala | Pro | Ala Ala | |
| | | 75 | | | | | 80 | | | | | 85 | | | 90 |
| GAC | GAC | GAC | AAG | GGC | CCC | CAG | CCG | CTT | CTG | CTC | CCG | CCG | TCC | GCC GCC | 760 |
| Asp | Asp | Asp | Lys | Gly | Pro | Gln | Pro | Leu | Leu | Leu | Pro | Pro | Ser | Ala Ala | |
| | | | | 95 | | | | | 100 | | | | | 105 | |
| CTG | GAC | GGG | GCC | AAG | GCT | GAC | GCA | CTT | GGA | GCC | AAA | GGC | GAG | CCA GGC | 808 |
| Leu | Asp | Gly | Ala | Lys | Ala | Asp | Ala | Leu | Gly | Ala | Lys | Gly | Glu | Pro Gly | |
| | | | 110 | | | | | 115 | | | | | 120 | | |
| GGC | GGG | CCT | GCG | GAG | CTG | GCG | CCC | GTC | GGG | CCG | GAC | GAG | AAG | GAG AAG | 856 |
| Gly | Gly | Pro | Ala | Glu | Leu | Ala | Pro | Val | Gly | Pro | Asp | Glu | Lys | Glu Lys | |
| | | 125 | | | | | 130 | | | | | 135 | | | |
| GGC | GCG | GGC | GCT | GGG | GGG | GAG | GAG | AAG | AAG | GGG | GCG | GGC | GAG | GGC GGC | 904 |
| Gly | Ala | Gly | Ala | Gly | Gly | Glu | Glu | Lys | Lys | Gly | Ala | Gly | Glu | Gly Gly | |
| | 140 | | | | | 145 | | | | | 150 | | | | |
| AAG | GAC | GGG | GAG | GGG | GGC | AAG | GAG | GGC | GAC | AAG | AAC | AAC | GGC | AAG TAC | 952 |
| Lys | Asp | Gly | Glu | Gly | Gly | Lys | Glu | Gly | Asp | Lys | Asn | Asn | Gly | Lys Tyr | |
| 155 | | | | | 160 | | | | | 165 | | | | | 170 |
| GAG | AAG | CCG | CCG | TTC | ACC | TAC | AAC | GCG | CTC | ATC | ATG | ATG | GCC | ATC AGG | 1000 |
| Glu | Lys | Pro | Pro | Phe | Thr | Tyr | Asn | Ala | Leu | Ile | Met | Met | Ala | Ile Arg | |
| | | | | 175 | | | | | 180 | | | | | 185 | |
| CAG | AGT | CCC | GAG | AAG | CGC | CTG | ACG | CTC | AAC | GGC | ATC | TAC | GAG | TTC ATC | 1048 |
| Gln | Ser | Pro | Glu | Lys | Arg | Leu | Thr | Leu | Asn | Gly | Ile | Tyr | Glu | Phe Ile | |
| | | | 190 | | | | | 195 | | | | | 200 | | |
| ATG | AAG | AAC | TTC | CCT | TAC | TAC | CGC | GAG | AAC | AAG | CAG | GGC | TGG | CAG AAC | 1096 |
| Met | Lys | Asn | Phe | Pro | Tyr | Tyr | Arg | Glu | Asn | Lys | Gln | Gly | Trp | Gln Asn | |
| | | 205 | | | | | 210 | | | | | 215 | | | |
| TCC | ATC | CGC | CAC | AAC | CTG | TCC | CTC | AAC | AAG | TGC | TTC | GTG | AAG | GTA CCG | 1144 |
| Ser | Ile | Arg | His | Asn | Leu | Ser | Leu | Asn | Lys | Cys | Phe | Val | Lys | Val Pro | |
| | | 220 | | | | | 225 | | | | | 230 | | | |
| CGC | CAC | TAC | GAC | GAC | CCG | GGC | AAG | GGC | AAC | TAC | TGG | ATG | CTG | GAC CCG | 1192 |
| Arg | His | Tyr | Asp | Asp | Pro | Gly | Lys | Gly | Asn | Tyr | Trp | Met | Leu | Asp Pro | |
| 235 | | | | | 240 | | | | | 245 | | | | | 250 |
| TCG | AGC | GAC | GAC | GTG | TTC | ATC | GGC | GGC | ACG | ACC | GGC | AAG | CTG | CGG CGC | 1240 |
| Ser | Ser | Asp | Asp | Val | Phe | Ile | Gly | Gly | Thr | Thr | Gly | Lys | Leu | Arg Arg | |
| | | | | 255 | | | | | 260 | | | | | 265 | |
| CGC | TCC | ACC | ACG | TCT | CGG | GCC | AAG | CTA | GCC | TTT | AAG | CGC | CGG | GCA CGG | 1288 |
| Arg | Ser | Thr | Thr | Ser | Arg | Ala | Lys | Leu | Ala | Phe | Lys | Arg | Arg | Ala Arg | |
| | | 270 | | | | | 275 | | | | | 280 | | | |
| CTC | ACC | TCC | ACC | GGC | CTC | ACC | TTC | ATG | GAC | CGC | GCC | GGC | TCC | CTC TAC | 1336 |
| Leu | Thr | Ser | Thr | Gly | Leu | Thr | Phe | Met | Asp | Arg | Ala | Gly | Ser | Leu Tyr | |
| | | 285 | | | | | 290 | | | | | 295 | | | |

| | | | | | | | | | | | | | | | | |
|---|---|---|---|---|---|---|---|---|---|---|---|---|---|---|---|---|
| TGG | CCC | ATG | TCG | CCC | TTC | CTG | TCC | CTG | CAC | CAC | CCT | CGC | GCC | AGC | AGC | 1384 |
| Trp | Pro | Met | Ser | Pro | Phe | Leu | Ser | Leu | His | His | Pro | Arg | Ala | Ser | Ser | |
| | 300 | | | | 305 | | | | | 310 | | | | | | |
| ACT | TTG | AGT | TAC | AAC | GGG | ACC | ACC | TCG | GCC | TAC | CCC | AGC | CAC | CCC | ATG | 1432 |
| Thr | Leu | Ser | Tyr | Asn | Gly | Thr | Thr | Ser | Ala | Tyr | Pro | Ser | His | Pro | Met | |
| 315 | | | | | 320 | | | | | 325 | | | | | 330 | |
| CCC | TAC | AGC | TCC | GTG | TTG | ACT | CAA | AAC | TCG | CTG | GGC | AAC | AAC | CAC | TCC | 1480 |
| Pro | Tyr | Ser | Ser | Val | Leu | Thr | Gln | Asn | Ser | Leu | Gly | Asn | Asn | His | Ser | |
| | | | | 335 | | | | | 340 | | | | | 345 | | |
| TTC | TCC | ACC | GCC | AAC | GGG | CTG | AGC | GTG | GAC | CGG | CTG | GTC | AAC | GGG | GAG | 1528 |
| Phe | Ser | Thr | Ala | Asn | Gly | Leu | Ser | Val | Asp | Arg | Leu | Val | Asn | Gly | Glu | |
| | | 350 | | | | | 355 | | | | | 360 | | | | |
| ATC | CCG | TAC | GCC | ACG | CAC | CAC | CTC | ACG | GCC | GCT | GCG | CTC | GCC | GCC | TCC | 1576 |
| Ile | Pro | Tyr | Ala | Thr | His | His | Leu | Thr | Ala | Ala | Ala | Leu | Ala | Ala | Ser | |
| | | 365 | | | | 370 | | | | | 375 | | | | | |
| GTG | CCC | TGC | GGC | CTG | TCG | GTG | CCC | TGC | TCC | GGG | ACC | TAC | TCC | CTC | AAC | 1624 |
| Val | Pro | Cys | Gly | Leu | Ser | Val | Pro | Cys | Ser | Gly | Thr | Tyr | Ser | Leu | Asn | |
| 380 | | | | | 385 | | | | | 390 | | | | | | |
| CCC | TGC | TCC | GTC | AAC | CTG | CTC | GCG | GGC | CAG | ACC | AGT | TAC | TTT | TTC | CCC | 1672 |
| Pro | Cys | Ser | Val | Asn | Leu | Leu | Ala | Gly | Gln | Thr | Ser | Tyr | Phe | Phe | Pro | |
| 395 | | | | 400 | | | | | 405 | | | | | 410 | | |
| CAC | GTC | CCG | CAC | CCG | TCA | ATG | ACT | TCG | CAG | ACC | AGC | ACG | TCC | ATG | AGC | 1720 |
| His | Val | Pro | His | Pro | Ser | Met | Thr | Ser | Gln | Thr | Ser | Thr | Ser | Met | Ser | |
| | | | | 415 | | | | | 420 | | | | | 425 | | |
| GCC | CGG | GCC | GCG | TCC | TCC | TCT | ACG | TCG | CCG | CAG | GCC | CCC | TCG | ACC | CTG | 1768 |
| Ala | Arg | Ala | Ala | Ser | Ser | Ser | Thr | Ser | Pro | Gln | Ala | Pro | Ser | Thr | Leu | |
| | | | 430 | | | | | 435 | | | | | 440 | | | |
| CCC | TGT | GAG | TCT | TTA | AGA | CCC | TCT | TTG | CCA | AGT | TTT | ACG | ACA | GGA | CTG | 1816 |
| Pro | Cys | Glu | Ser | Leu | Arg | Pro | Ser | Leu | Pro | Ser | Phe | Thr | Thr | Gly | Leu | |
| | | 445 | | | | | 450 | | | | | 455 | | | | |
| TCC | GGG | GGA | CTG | TCT | GAT | TAT | TTC | ACA | CAT | CAA | AAT | CAG | GGG | TCT | TCT | 1864 |
| Ser | Gly | Gly | Leu | Ser | Asp | Tyr | Phe | Thr | His | Gln | Asn | Gln | Gly | Ser | Ser | |
| | 460 | | | | | 465 | | | | | 470 | | | | | |
| TCC | AAC | CCT | TTA | ATA | CAT | TAACATCCCG | GGGACCAGAC | TGTAAGTGAA | | | | | | | | 1912 |
| Ser | Asn | Pro | Leu | Ile | His | | | | | | | | | | | |
| 475 | | | | | 480 | | | | | | | | | | | |

| | | | | |
|---|---|---|---|---|
| CGTTTTACAC | ACATTTGCAT | TGTAAATGAT | AATTAAAAAA | TAAGTCCAGG | TATTTTTTAT | 1972 |
| TAAGCCCTTC | CCCCCATTTC | TGTACGTTTG | TTCAGTCTTT | AGGGTTGTTT | ACTATTCTAA | 2032 |
| CACGGTGTGG | AGTGTCAGCA | GCGAGGTGCA | ATGTGGGAGA | ATACATTGTA | GAATATAAGG | 2092 |
| TTTGGACGTC | AAATTATAGT | AGAATGTGTA | TCTAAATAGT | GACTGCTTTG | CCATTTCATT | 2152 |
| CAAACCTGAC | AAGTCTATCT | CTAAAGGCTG | CCAGATTTCC | ATGTGTGCAG | TATTATAAGT | 2212 |
| TATCATGGAT | CTATCTGGTG | GACGCAGGCC | TTGAAGAACA | ACCTAAATTA | TGAAGAGAGT | 2272 |
| TTTAAAATGT | TAAACTGTAA | TTTGAATGTA | AGAATTTGTA | GGTAAAGGTG | CCCAAGAAAT | 2332 |
| TATATTGGCC | ATTTATTGTT | TTGTCCTTTT | CTTTAAAGAA | CTGTTTTTTT | CTTTTGTTTA | 2392 |
| CTTTTAGACC | AAAGATTGGA | TTCTAGCAAA | TGCACTTGGT | ATACTAAGTA | TTAAAACAAG | 2452 |
| CAAACAAACA | AACAAAAAAA | GGAAGGTTGT | TTAGTTTGGC | AACACTGCCC | ATTCAATTGA | 2512 |
| ATCCGAAAGG | ACAAAATTAA | GGATTGCCTT | CAGTTTGTGT | TGTGTATATT | TCGATGTATG | 2572 |
| TGGTCACTAA | CAGGTCACTT | TATTTTTTCT | AAATGTAGTG | AAATGTTAAT | ACCTATTGTA | 2632 |
| CTTATAGGTA | AACCTTGCAA | ATATGTAACC | TGTGTTGCGC | AAATGCCGCA | TCAATTTGAG | 2692 |
| TGATTGTTAA | TGTTGCTTAA | AAATTCTTGA | TTGTGATACT | GTGGTCATAT | GCCCTTGTTT | 2752 |
| GTCACTTACA | AAAATGTTTA | CTATGAACAC | ACAGAAATAA | AAAATAGGCT | AAATTCATAT | 2812 |
| ATAAAAAAAA | AAAAAAA | | | | | 2830 |

( 2 ) INFORMATION FOR SEQ ID NO:2:

( i ) SEQUENCE CHARACTERISTICS:
    ( A ) LENGTH: 480 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

```
Met Leu Asp Met Gly Asp Arg Lys Glu Val Lys Met Ile Pro Lys Ser
 1               5                  10                  15

Ser Phe Ser Ile Asn Ser Leu Val Pro Glu Ala Val Gln Asn Asp Asn
                20                  25                  30

His His Ala Ser His Gly Tyr His Asn Ser His His Pro Gln His His
            35                  40                  45

His His His His His His His His Pro Pro Pro Pro Ala Pro Gln Pro
        50                  55                  60

Pro Pro Pro Pro Pro Gln Gln Gln Gln Pro Pro Ala Pro Gln
 65                  70                  75                  80

Pro Pro Gln Ala Arg Gly Ala Pro Ala Ala Asp Asp Asp Lys Gly Pro
                85                  90                  95

Gln Pro Leu Leu Leu Pro Pro Ser Ala Ala Leu Asp Gly Ala Lys Ala
                100                 105                 110

Asp Ala Leu Gly Ala Lys Gly Glu Pro Gly Gly Gly Pro Ala Glu Leu
            115                 120                 125

Ala Pro Val Gly Pro Asp Glu Lys Glu Lys Gly Ala Gly Ala Gly Gly
    130                 135                 140

Glu Glu Lys Lys Gly Ala Gly Glu Gly Gly Lys Asp Gly Glu Gly Gly
145                 150                 155                 160

Lys Glu Gly Asp Lys Asn Asn Gly Lys Tyr Glu Lys Pro Pro Phe Thr
                165                 170                 175

Tyr Asn Ala Leu Ile Met Met Ala Ile Arg Gln Ser Pro Glu Lys Arg
                180                 185                 190

Leu Thr Leu Asn Gly Ile Tyr Glu Phe Ile Met Lys Asn Phe Pro Tyr
            195                 200                 205

Tyr Arg Glu Asn Lys Gln Gly Trp Gln Asn Ser Ile Arg His Asn Leu
    210                 215                 220

Ser Leu Asn Lys Cys Phe Val Lys Val Pro Arg His Tyr Asp Asp Pro
225                 230                 235                 240

Gly Lys Gly Asn Tyr Trp Met Leu Asp Pro Ser Ser Asp Asp Val Phe
                245                 250                 255

Ile Gly Gly Thr Thr Gly Lys Leu Arg Arg Arg Ser Thr Thr Ser Arg
            260                 265                 270

Ala Lys Leu Ala Phe Lys Arg Arg Ala Arg Leu Thr Ser Thr Gly Leu
    275                 280                 285

Thr Phe Met Asp Arg Ala Gly Ser Leu Tyr Trp Pro Met Ser Pro Phe
290                 295                 300

Leu Ser Leu His His Pro Arg Ala Ser Ser Thr Leu Ser Tyr Asn Gly
305                 310                 315                 320

Thr Thr Ser Ala Tyr Pro Ser His Pro Met Pro Tyr Ser Ser Val Leu
                325                 330                 335

Thr Gln Asn Ser Leu Gly Asn Asn His Ser Phe Ser Thr Ala Asn Gly
            340                 345                 350

Leu Ser Val Asp Arg Leu Val Asn Gly Glu Ile Pro Tyr Ala Thr His
    355                 360                 365

His Leu Thr Ala Ala Ala Leu Ala Ala Ser Val Pro Cys Gly Leu Ser
370                 375                 380
```

| | | | | | | | | | | | | | | |
|---|---|---|---|---|---|---|---|---|---|---|---|---|---|---|
| Val 385 | Pro | Cys | Ser | Gly | Thr 390 | Tyr | Ser | Leu | Asn | Pro 395 | Cys | Ser | Val | Asn | Leu 400 |
| Leu | Ala | Gly | Gln | Thr 405 | Ser | Tyr | Phe | Phe | Pro 410 | His | Val | Pro | His 415 | Pro | Ser |
| Met | Thr | Ser | Gln 420 | Thr | Ser | Thr | Ser | Met 425 | Ser | Ala | Arg | Ala | Ala 430 | Ser | Ser |
| Ser | Thr | Ser 435 | Pro | Gln | Ala | Pro | Ser 440 | Thr | Leu | Pro | Cys | Glu 445 | Ser | Leu | Arg |
| Pro | Ser 450 | Leu | Pro | Ser | Phe | Thr 455 | Thr | Gly | Leu | Ser | Gly 460 | Gly | Leu | Ser | Asp |
| Tyr 465 | Phe | Thr | His | Gln | Asn 470 | Gln | Gly | Ser | Ser | Ser 475 | Asn | Pro | Leu | Ile | His 480 |